(12) United States Patent
Nagamatsu et al.

(10) Patent No.: US 12,054,747 B2
(45) Date of Patent: Aug. 6, 2024

(54) METHOD OF DIFFERENTIATING PRIMORDIAL GERM CELL INTO PRIMORDIAL FOLLICLE IN VITRO

(71) Applicant: KYUSHU UNIVERSITY, NATIONAL UNIVERSITY CORPORATION, Fukuoka (JP)

(72) Inventors: Go Nagamatsu, Fukuoka (JP); Yohei Nishimura, Fukuoka (JP); So Shimamoto, Fukuoka (JP); Katsuhiko Hayashi, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 630 days.

(21) Appl. No.: 17/253,518

(22) PCT Filed: May 29, 2019

(86) PCT No.: PCT/JP2019/021209
§ 371 (c)(1),
(2) Date: Dec. 17, 2020

(87) PCT Pub. No.: WO2019/244581
PCT Pub. Date: Dec. 26, 2019

(65) Prior Publication Data
US 2021/0261922 A1 Aug. 26, 2021

(30) Foreign Application Priority Data
Jun. 21, 2018 (JP) ................................ 2018-117988

(51) Int. Cl.
*C12N 5/071* (2010.01)
*C12N 5/075* (2010.01)

(52) U.S. Cl.
CPC ......... *C12N 5/0682* (2013.01); *C12N 5/0609* (2013.01); *C12N 2500/02* (2013.01); *C12N 2501/40* (2013.01); *C12N 2501/727* (2013.01); *C12N 2506/04* (2013.01); *C12N 2521/00* (2013.01)

(58) Field of Classification Search
CPC ............. C12N 5/0682; C12N 5/0611; C12N 2506/04; C12N 2521/00
See application file for complete search history.

(56) References Cited

U.S. PATENT DOCUMENTS

| 7,671,027 B2 * | 3/2010 | Loumaye | A61K 38/09 530/398 |
| 2014/0314762 A1 * | 10/2014 | Cheng | A61K 38/2242 435/375 |
| 2018/0251729 A1 * | 9/2018 | Obata | C12N 5/0611 |

FOREIGN PATENT DOCUMENTS

| WO | WO-2017013412 A1 * | 1/2017 | ............ B01D 5/00 |
| WO | WO 2017/047799 A1 | 3/2017 | |

OTHER PUBLICATIONS

Extended European Search Report for European Patent Application No. 19822475.0, mailed Feb. 21, 2022.
Hayashi et al., "Reconstitution of the Mouse Germ Cell Specification Pathway in Culture by Pluripotent Stem Cells", Cell, Jun. 2011, 146(4): 519-532.
Nagamatsu et al., "Mechanical stress accompanied with nuclear rotation is involved in the dormant state of mouse oocytes", Science Advances, Jun. 26, 2019, 5: eaav9960, XP055890259, Retrieved from url: https://www.science.org/doi/epdf/10.1126/sciadv.aav9960.
Shimamoto et al., "Hypoxia induces the dormant state in oocytes through expression of Foxo3", Proceedings of the National Academy of Sciences, Jun. 18, 2019, 116(25): 12321-12326.
Kanako Morohakua et al., Complete in vitro generation of fertile oocytes from mouse primordial germ cells, PNAS, vol. 113, No. 32, 9021-9026. (2016).
Pilar Lopez-Iglesias et al., Hypoxia Induces Pluripotency in Primordial Germ Cells by HIF1α Stabilization and Oct4 Deregulation, Antioxidants & Redox Signaling, vol. 22, No. 3, pp. 205-223. (2015).
Hikabe et al., "Reconstitution in vitro of the entire cycle of the mouse female germline", Nature 539:299-303 (2016).
Hirao, "oocytes expulsion", Tatsumi University Journal 29:112-113 (2017).
International Search Report for International Application No. PCT/JP2019/021209 mailed Aug. 20, 2019, 4 pages.

* cited by examiner

*Primary Examiner* — Marcia S Noble
(74) *Attorney, Agent, or Firm* — Lathrop GPM LLP; Brian C. Trinque

(57) ABSTRACT

A method of differentiating a primordial germ cell into a primordial follicle in vitro includes culturing a primordial germ cell and a supporting cell adjacent to the primordial germ cell under a pressurized condition or a low oxygen concentration condition.

9 Claims, 10 Drawing Sheets

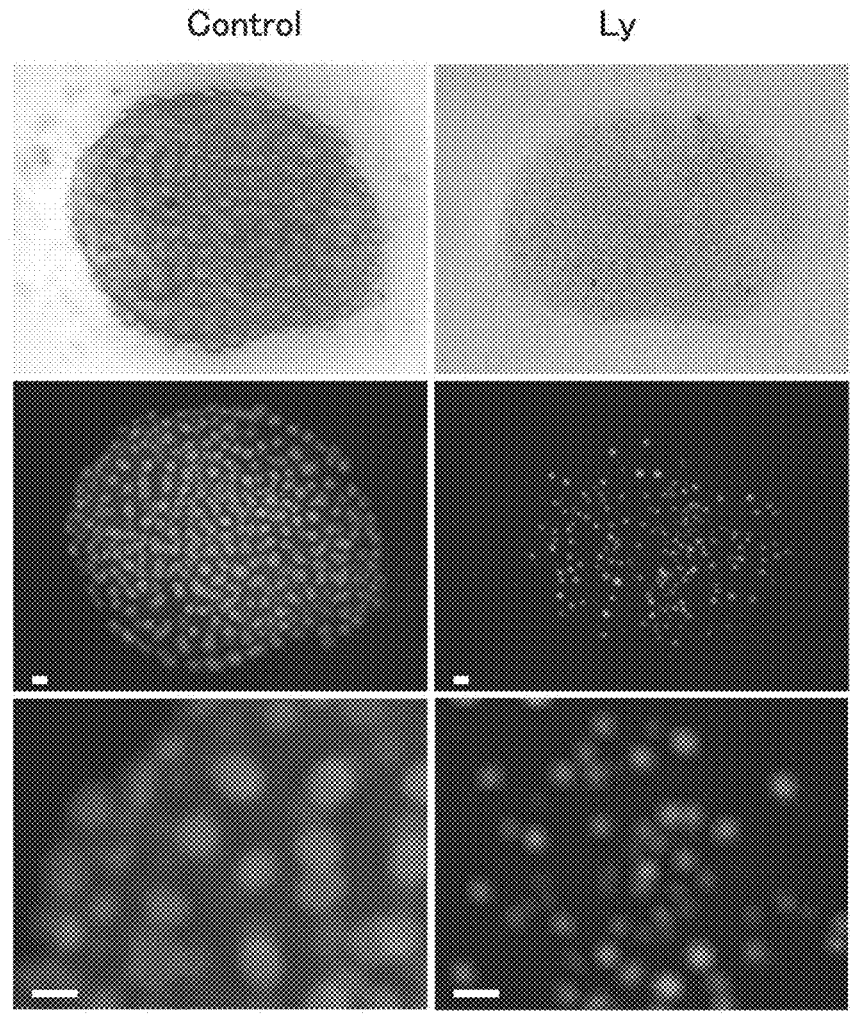

METHOD OF DIFFERENTIATING PRIMORDIAL GERM CELL INTO PRIMORDIAL FOLLICLE IN VITRO

TECHNICAL FIELD

The present invention relates to a method of differentiating a primordial germ cell into a primordial follicle in vitro. Priority is claimed on Japanese Patent Application No. 2018-117988, filed on Jun. 21, 2018, the content of which is incorporated herein by reference.

BACKGROUND ART

Somatic cells that make up the body and germ cells that carry genetic information to a next generation are present in the living body. In particular, an egg which is a female germ cell is an important cell that plays a role in carrying out early development. The female germ cell in mammals undergoes meiosis after proliferation of primordial germ cells during an embryonic period, and undergoes most cell death almost at the same time as birth. Surviving oocytes form a primordial follicle with surrounding granulosa cells. In this manner, the female germ cells decreases after peaking in primordial germ cells during the embryonic period, and after birth, while maintaining a limited number of oocytes, some of the cells are periodically activated to maintain an ovulation cycle. The primordial follicle is a base point of the ovulation cycle and is present in an ovarian cortex in a state where the oocytes are surrounded by a single layer of more flat granulosa cells. In addition, in the ovulation cycle, primordial follicles develop as primary follicles, secondary follicles, antral follicles, and Graffian follicles (mature follicles) to cause ovulation. However, the entire mechanism of maintenance and activation of primordial follicles has not yet been clarified. Therefore, the establishment of an in vitro culture method for differentiating primordial follicles from primordial germ cells can be an approach to elucidate the mechanism of maintenance and activation of the primordial follicles. Furthermore, when such a culture method can be established, continuous oogenesis in vivo and in vitro becomes possible.

In recent years, a culture method for differentiating primordial germ cells into functionally mature oocytes has been established (see, for example, Patent Document 1 and Non Patent Document 1).

PRIOR ART LITERATURE

Patent Documents

Patent Document 1: PCT International Publication No. WO 2017/047799

Non-Patent Document

Non-Patent Document 1: Morohaku K. et al., "Complete in vitro generation of fertile oocytes from mouse primordial germ cells.", Proc Natl Acad Sci, Vol. 113, No. 32, p9021-9026, 2016.

DISCLOSURE OF INVENTION

Problems to be Solved by the Invention

However, in methods described in Patent Document 1 and Non Patent Document 1, the formation of a primordial follicle was not confirmed, and functional oogenesis was transient.

The present invention has been made in view of the above circumstances, and provides a method of differentiating a primordial germ cell into a primordial follicle in vitro.

Means for Solving the Problems

As a result of repeated intensive study to achieve the above object, the inventors have found that a primordial follicle can be formed by culturing a primordial germ cell and a supporting cell adjacent to the primordial germ cell under a pressurized condition or a low oxygen concentration condition, and have completed the present invention.

That is, the present invention includes the following aspects.

A method according to a first aspect of the present invention is a method of differentiating a primordial germ cell into a primordial follicle in vitro, the method including culturing a primordial germ cell and a supporting cell adjacent to the primordial germ cell under a pressurized condition or a low oxygen concentration condition.

In the method according to the first aspect, the culturing may be carried out under the pressurized condition and the low oxygen concentration condition.

In the method according to the first aspect, the culturing may be carried out in presence of a PI3 kinase inhibitor.

In the method according to the first aspect, the PI3 kinase inhibitor may be LY294002.

In the method according to the first aspect, the culturing may be carried out under a condition in which an influence of estrogen or a factor having a function similar to a function of the estrogen is eliminated.

In the method according to the first aspect, the low oxygen concentration condition may be a condition in which an oxygen concentration in a culture atmosphere is 7% or lower.

In the method according to the first aspect, the low oxygen concentration condition may be a condition in which an oxygen concentration in a culture atmosphere is 3% or higher and 7% or lower.

In the method according to the first aspect, the pressurized condition may be a condition of higher than 23 kPa and 40 kPa or lower.

In the method according to the first aspect, the pressurized condition may be a condition of 28 kPa or higher and 38 kPa or lower.

In the method according to the first aspect, the obtained primordial follicle may satisfy conditions of (1) and (2) below:
 (1) an oocyte is surrounded by flat granulosa cells;
 (2) a transcription factor having a function of maintaining follicle maturation in a resting phase is localized in a nucleus of the oocyte.

In the method according to the first aspect, the transcription factor may be Foxo3a.

In the method according to the first aspect, the obtained primordial follicle may further satisfy a condition of (3) below:
 (3) a diameter is 20 µm or smaller.

Effects of the Invention

According to the method of the aspect, it is possible to differentiate a primordial germ cell into a primordial follicle in vitro.

BRIEF DESCRIPTION OF THE DRAWINGS

FIG. 6A shows captured images, taken by a fluorescent stereomicroscope, of gonad sections which were obtained by culturing gonads of 12.5 day-old female mouse after fertilization, adding LY294002 (hereinafter, may be abbreviated as "Ly") which is a PI3K inhibitor from the 6th day from the start of the culturing, and collecting the gonad sections on the 16th day from the start of the culturing in Reference Example 2. Upper drawings are bright field images, middle drawings are fluorescence images, and lower drawings are enlarged images respectively of the middle drawings. In the middle and lower drawings, the oocytes were visualized by the fluorescence of CFP expressed under the control of the expression of Stella, which is the oocyte marker. A scale bar represents 50 μm.

EMBODIMENTS FOR CARRYING OUT THE INVENTION

Figure 1:
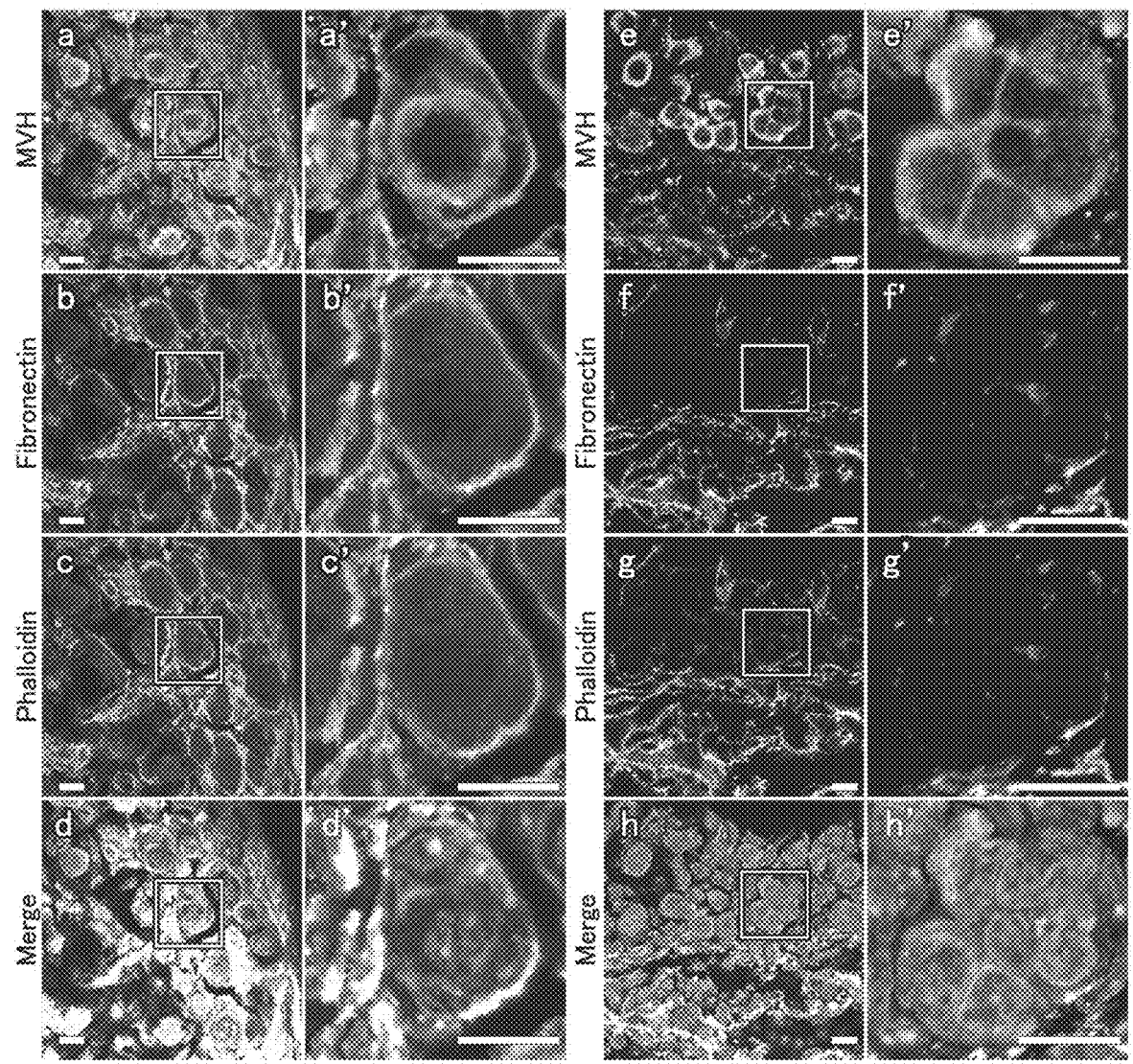
FIG. 1 shows a to d which are immunostaining images of gonad sections of 3.5-day-old female mouse in Reference Example 1. A scale bar represents 10 μm. a is an immunostaining image using an antibody against Mouse Vasa homolog (MVH) of a germ cell marker. b is an immunostaining image using an antibody against fibronectin, which is an extracellular matrix. c is a staining image using Alexa Fluor 488-labeled phalloidin that specifically binds to F-actin which is a stress fiber. In addition, d is an image in which a nuclear-staining image using 4',6-diamidino-2-phenylindole (DAPI) is superimposed on the staining images in a to c. In addition, a' to d' are magnified images of portions surrounded by squares in a to d, respectively. A scale bar represents 10 μm. e to h are immunostaining images of gonad sections of 12.5-day-old female mouse after fertilization in Reference Example 1. A scale bar represents 10 μm. e is an immunostaining image using an antibody against the MVH of a germ cell marker. f is an immunostaining image using an antibody against fibronectin, which is an extracellular matrix. g is an immunostaining image using an antibody against F-actin, which is a stress fiber. In addition, h is an image in which a nuclear-staining image using DAPI is superimposed on the immunostaining images in a to c. In addition, e' to h' which are magnified images of portions surrounded by squares in e to h, respectively.

<Method of differentiating primordial germ cell into primordial follicle in vitro>

A method according to the present embodiment is a method of differentiating a primordial germ cell into a primordial follicle in vitro, the method including culturing a primordial germ cell and a supporting cell adjacent to the primordial germ cell under a pressurized condition or a low oxygen concentration condition. In addition, the culturing step may be referred to as a "step (A)" below.

According to the method of the present embodiment, it is possible to differentiate a primordial germ cell into a primordial follicle in vitro.

In the in vitro culture method of the related art, the formation of a primordial follicle was not confirmed, and functional oogenesis was transient. On the other hand, according to the method of the present embodiment, the primordial germ cell and the supporting cell adjacent to the primordial germ cell can be efficiently differentiated into a primordial follicle. In addition, it is difficult to return highly differentiated follicles such as primary follicles and secondary follicles to the womb to induce differentiation, whereas the primordial follicle can be returned to the womb to induce differentiation. Therefore, according to the method of the present embodiment, sustainable oogenesis becomes possible. The "follicle" referred to here includes an egg cell and a somatic cell (granulosa cell and capsule cell) surrounding the egg cell. In addition, the method of the present embodiment can be useful for elucidating the mechanism of maintenance and activation of oocytes.

Note that, in the present specification, a "primordial germ cell" refers to a cell which is planned to differentiate into a germ cell, and finally differentiates into an egg or a sperm through meiosis.

The primordial germ cell may be derived from a living body, or may be a primordial germ cell like cell (PGCLC) that has been induced to differentiate from a pluripotent stem cell. When the primordial germ cells are collected from a living body, for example, the primordial germ cells can be collected together with a gonad from a female mouse fetus (from 11.5 to 12.5 days old). When the gonads are collected from the living body, the gonads may be collected together with the mesonephros, or the mesonephros may be separated or collected.

Further, as described above, in the present specification, the "primordial germ cell" includes a primordial germ cell like cell differentiated from a pluripotent stem cell. Here, the "pluripotent stem cell" refers to an undifferentiated cell having "self-renewal ability" capable of proliferating while maintaining an undifferentiated state and "differentiation pluripotency" capable of differentiating into all three germ layer lines. The pluripotent stem cell is not limited to the followings, and examples thereof include induced pluripotent stem cells (iPS cells), embryonic stem cells (ES cells), embryonic germ cells derived from primordial germ cells (EG cells), and testis tissue. Examples thereof include multipotent germline STEM cells (mGS cells) isolated in the process of establishing and culturing GS cells from, and Muse cells isolated from bone marrow mesenchymal cells. The ES cell may be an ES cell generated by nuclear reprogramming from a somatic cell. The pluripotent stem cells listed above can be obtained by known methods.

The term "iPS cell" as used herein refers to a cell that can be reprogrammed into cells of various tissues and organs by introducing some genes into differentiated somatic cells. In the method of the present embodiment, the iPS cells used for inducing differentiation of primordial germ cells may be derived from primary cultured cells of somatic cells collected from an appropriate donor, or may be derived from an established cell line. Since iPS cells can induce differentiation into any germ layer cells, the somatic cells used for preparing iPS cells may be, in principle, derived from either ectoderm or endoderm cells. Cells in skin, hair, gingiva, blood, or the like which are less invasive and easy to collect, and are suitable as somatic cells used for the preparation of iPS cells. As for the method of preparing iPS cells, a method known in the art may be followed. Specifically, for example, the preparation methods described in known references such as "Okita K. et al.," Generation of germline-competent induced pluripotent stem cells. ", Nature, Vol. 448, $p^{313}$-317, 2007." (Reference 1), and "Hamanaka S. et al., "Generation of germline-competent rat induced pluripotent stem cells.", PLoS One, Vol. 6, Issue 7, e22008, 2011." (Reference 2) are available.

Further, in the method of the present embodiment, ES cells used for inducing differentiation of primordial germ cells can be obtained by a known method. For example, it can be established by collecting an inner cell mass from the blastocyst of a fertilized egg of a target animal and culturing the inner cell mass on a feeder cell derived from fibroblasts. In addition, ES cells established by culturing an early embryo produced by nuclear transplantation of a nucleus of a somatic cell can also be used.

In addition, a method of inducing differentiation of primordial germ cell like cells from iPS cells or ES cells can be performed by referring to a known method, for example, Hayashi K. et al., "Reconstitution of the mouse germ cell specification pathway in culture by pluripotent stem cells.", Cell, Vol. 146, No. 4, p519-532, 2011." (Reference 3) or the like.

In a case where pluripotent stem cell-derived PGCLC is used as the primordial germ cell, it is preferable to remove undifferentiated cells from the differentiation-induced pluripotent stem cell population in advance. Such a method is known. For example, by introducing a nucleic acid encoding a fusion protein in which Blimp1, which is a marker gene of primordial germ cells, and a reporter protein are bound, to pluripotent stem cells, PGCLC induced to be differentiated from pluripotent stem cells and undifferentiated cells can be easily separated by a Fluorescence-activated cell sorting (FACS) method or the like.

Here, the "primordial germ cells" in the present specification are primordial germ cells derived from living body and primordial germ cell like cells derived from pluripotent stem cells listed above, and also includes cells in which the gene of the cell is modified by using a genetic engineering technique.

As a method of modifying the genes of primordial germ cells derived from living body and primordial germ cell like cells derived from pluripotent stem cells, known genome editing methods such as a method using a CRISPR system, a Transcription Activator-Like Effector Nucleases (TALEN), and a method using zinc finger nuclease, and a homologous recombination method are used. Accordingly, it is possible to introduce the target nucleic acid, vector, or the like. Examples of the method of introducing a nucleic acid, a vector, or the like include a microinjection method (microinjection), an electroporation method, a lipofection method, and a nucleic acid introduction method using a viral vector. Further, the method of introducing a foreign gene or a foreign nucleic acid fragment is not limited to the methods listed above as long as the genetically modified primordial germ cell can be differentiated into a functional oocyte by the method of the present embodiment.

The gene modification to the primordial germ cell can be performed at an appropriate timing during the culture period of the primordial germ cell. For example, in a mouse, the gene modification can be performed during the period from 11.5 to 12.5 days old. Also, in a case where primordial germ cell like cells derived from pluripotent stem cells are used, the pluripotent stem cells before the induction of differentiation into primordial germ cell like cells can be genetically modified by a known method.

Further, in the present specification, the "supporting cell" refers to cells surrounding a primordial germ cell, and in a sexually differentiated ovary, cells that differentiate into granulosa cells or capsule cells. The supporting cells will be used for co-culture of primordial germ cells in the future because the supporting cells will differentiate into granulosa cells and capsule cells that make up follicles. Therefore, it is preferable to culture the primordial germ cells in a manner that a gonad is cultured as it is, or co-cultured so that the primordial germ cell and the supporting cell are in contact with each other. In addition, when pluripotent stem cell-derived PGCLC is used as a primordial germ cell, somatic cells derived from the gonad collected from a living body can be used as a supporting cell.

When using somatic cells derived from the gonad collected from a living body as supporting cells, it is preferable to carry out a culturing step for producing an aggregate including pluripotent stem cell-derived PGCLC and somatic cells derived from the gonad, in advance, prior to the step (A).

The method of collecting somatic cells derived from the gonad and the method of producing an aggregate including pluripotent stem cell-derived PGCLC and somatic cells derived from the gonad can be performed according to the method described in Reference 3.

For example, in the method of collecting somatic cells derived from the gonad, the gonad can be surgically collected from a living body, and the somatic cells configuring the gonad can be dissected by trypsin treatment or the like. In this case, it is preferable to remove the germ cells inherent in the gonad derived from the living body. The method of removing the germ cells in the gonad can be carried out by a known method. For example, the inherent germ cells can be removed by a Magnetic activated cell sorting method using an anti-SSEA1 antibody or an anti-CD31 antibody. Here, the gonad for collecting the somatic cells as supporting cells are preferably derived from the fetus. In the case of a mouse, for example, a gonad derived from a mouse fetus with a fetal age of 12.5 days (also referred to as "fetus age") can be used. In addition, a person skilled in the art can appropriately select the gonad at a preferable time depending on the animal species from which the gonad is derived, based on the present disclosure and common general knowledge in the art.

In addition, a method of producing an aggregate including pluripotent stem cell-derived PGCLC and somatic cells derived from the gonad can be carried out by, for example, mixing, aggregating, and culturing pluripotent stem cell-derived PGCLC and somatic cells derived from the gonad in a GK15 medium containing Retinoic Acid (a medium obtained by adding 15% KSR in GMEM (KnockOut (registered trademark) Serum Replacement), 1×GlutaMax (registered trademark), 1×penicillin/streptomycin (100 U/mL Penicillin and 0.1 mg/mL streptomycin), 100 µM 2-mercaptoethanol (2ME), and 1 µM Reproductive Acid to GMEM). It is preferable to use a culture dish with low adsorption for culturing.

In the case of the mouse, for example, the culture period for producing aggregates can be approximately 2 days or more and 3 days or less, preferably 2 days. Further, those skilled in the art can appropriately set a preferable culture period depending on the animal species from which the cells are derived.

In addition, the ratio of pluripotent stem cell-derived PGCLC to somatic cells derived from the gonad is not limited as long as the produced aggregates form primordial follicles, and in the case of the mouse, for example, the ratio of the number of pluripotent stem cell-derived PGCLCs to the somatic cells derived from the gonad is preferably set to about 1:10.

Also, as the primordial germ cells and supporting cells, or the gonad containing the primordial germ cells and supporting cells, those that have been cryopreserved can also be used. The cryopreservation method can be carried out by a known method. For example, cryopreservation of primordial germ cells and supporting cells can be performed by a slow freezing method using a 10% DMSO solution or a commercially available freezing agent (such as Celbanker (registered trademark)).

As the primordial germ cells used in the method of the present embodiment, those derived from mammals are used. Examples of the mammals include humans, chimpanzees and other primates; livestock animals such as dogs, cats, rabbits, horses, sheep, goats, cows, pigs, rats (including nude rats), mice (including nude and skid mice), hamsters, guinea pigs; pet animals; and experimental animals, but are not limited thereto.

Next, steps of the method of the present embodiment will be described in detail below.

<Step (A)>

In step (A), a primordial germ cell and a supporting cell adjacent to the primordial germ cell are cultured under a pressurized condition or a low oxygen concentration condition to form primordial follicle. Also, in a case where the gonad collected from the living body is used in the step (A), it is not necessary to isolate the primordial germ cell and the supporting cell from the gonad, and it is possible to culture the gonad as it is or as aggregates of the isolated primordial germ cell and the supporting cells or as a several tissue sections.

Also, in the present specification, when the expression "culture of primordial germ cells and supporting cells adjacent to the primordial germ cells" in the step (A) is used, the expression includes a case of culturing gonad containing the primordial germ cell and the supporting cell, aggregates of the isolated primordial germ cells and the supporting cells, or a portion thereof. As long as the primordial follicles can be obtained, the primordial germ cells and the supporting cells can be isolated from the gonad and cultured. In addition, in a case of using the primordial germ cell like cells derived from pluripotent stem cells, as described above, it is preferable to prepare in advance an aggregate including the pluripotent stem cell-derived PGCLC and somatic cells derived from the gonad in advance.

Specifically, as the pressurized condition, a condition in which a culture solution containing the primordial germ cell or the supporting cell or containing a gonad containing the primordial germ cell and the supporting cell is applied with a hydrostatic pressure of higher than 23 kPa and 40 kPa or lower is preferable, a condition in which the hydrostatic pressure of 28 kPa or higher and 38 kPa or lower is applied is more preferable, a condition in which the hydrostatic pressure of 30 kPa or higher and 35 kPa or lower is applied is still more preferable, and a condition in which the hydrostatic pressure of 32 kPa or higher and 34 kPa or lower is applied is particularly preferable.

When the hydrostatic pressure to be applied is within the above range, the primordial germ cells can be more efficiently differentiated into primordial follicles.

Also, as the pressurization method, for example, as described in Examples to be described later, a method using a commercially available pressurization culture device such as AGP-3001S (registered trademark) of STREX can be mentioned.

Specifically, as the low oxygen concentration condition, regarding the oxygen concentration in the culture atmosphere, a condition of 7% or lower is preferable, a condition of 3% or higher and 7% or lower is more preferable, and a condition of 4% or higher and 6% or lower is still more preferable, and a condition of 5% is particularly preferable.

When the oxygen concentration is within the above range, the primordial germ cells can be more efficiently differentiated into primordial follicles.

Also, as a culture method under the low oxygen concentration condition, for example, as described in Examples to be described later, a culture method using a commercially available incubator capable of adjusting the oxygen concentration such as APM30D manufactured by Astec Co., Ltd. can be mentioned.

As the time at which the pressurized condition and the low oxygen concentration condition are started, the conditions may be started at the start time of culturing the primordial germ cell and the supporting cell adjacent to the primordial germ cell, and may be started in the middle of culturing according to the time when the formation of the primordial follicle is started.

Also, in the step (A), the culture temperature can be, for example, 25° C. or higher and 40° C. or lower, and for example, 30° C. or higher and 37° C. or lower.

The culture period for forming atomic follicles from primordial germ cells varies depending on the animal species from which the primordial germ cells to be cultured are derived, but it is preferable that the period until the primordial germ cells form atomic follicles in vivo is used as a guide. In a case of culturing the mouse primordial germ cells, it is preferable to culture the mouse primordial germ cells for a number of days corresponding to around 10 days after birth. For example, in a case where the primordial germ cells are collected from a female mouse fetus with a fetal age of 12.5 days and started to culture, the culture period is preferably 14 days or more and 21 days or less, more preferably 16 days or more and 21 days or less, and still more preferably 18 days or more and 21 days or less. In addition, when culturing the aggregates of the pluripotent stem cell-derived PGCLC and somatic cells of mouse, it is preferable that the number of days is 11 days or more and 21 days or less counting from the start of culturing the aggregates prepared in advance.

As a medium to be used, a known basal medium can be used, and examples thereof include α-MEM, PRMI1640, 199, and StemPro (registered trademark)-34 SFM, and these basal media can be used by adding serum or alternative serum thereto. However, the basal medium used in the step (A) is not limited to those listed above as long as the primordial germ cells differentiate into primordial follicles. The basal medium may appropriately contain other components such as ascorbic acid and penicillin as long as other components do not interfere with the differentiation of primordial germ cells into primordial follicles.

In addition, in a culture for forming a primordial follicle from a primordial germ cell, two or more of the basal media as listed above can be used in combination. For example, α-MEM can be used as the basal medium for the first half culture for forming primordial follicles from primordial germ cells, and StemPro (registered trademark)-34 SFM can be used as the basal medium for the second half culture. Basically, the formation of primordial follicles from primordial germ cells can be achieved by using one basal medium, but by changing the basal medium used, the proliferation of granulosa cells can be further promoted, and the follicle structure is less likely to be broken when the formed primordial follicles is isolated, which is preferable. Such an effect of further promoting the proliferation of granulosa cells is particularly desirable in a case where primordial follicles are formed from cell aggregates of pluripotent stem cell-derived PGCLC and the somatic cells derived from the gonad. For example, in a case where two basal media of the α-MEM and the StemPro (registered trademark)-34 SFM are used in culturing the cell aggregates of mouse pluripotent stem cell-derived PGCLC and somatic cells derived from the gonad, the medium can be replaced from the α-MEM to the StemPro (registered trademark)-34 SFM from the 4th day to the 8th day after the start of culturing the aggregates, and the 4th day after the start of the culture is more preferable. In addition, even in a case of culturing the primordial germ cells derived from the gonad of mouse, the medium can be replaced at the same time.

Also, as described above, the culture temperature, the culture period and the medium to be used have been exemplified, but those skilled in the art can appropriately set a preferable culture temperature, the culture period and the type of medium to be used, depending on the animal species from which the cells are derived.

In addition, the culture of primordial germ cells in the step (A) is preferably carried out using a known insert membrane such as a Transwell-COL membrane in a culture dish such as a 6-well plate. In addition, during the culture period, it is preferable to replace about half of the medium used for culturing with a new medium every other day. Those skilled in the art can appropriately design and carry out the culture dish, insert membrane, timing of medium replacement, and the like, depending on the animal species from which the primordial germ cells to be cultured are derived.

In addition, in the method according to the present embodiment, the step (A) may be carried out under the pressurized condition and the low oxygen concentration condition. Accordingly, the primordial germ cells can be more efficiently differentiated into primordial follicles. In addition, as shown in Examples to be described later, there is a tendency that the proportion of oocytes having a smaller size is larger than that in a case of performing the culture under pressurized condition or low oxygen concentration condition.

Also, in the method of the present embodiment, the step (A) may be carried out under the pressurized condition or low oxygen concentration condition, and further in the presence of a PI3 kinase inhibitor.

In general, the "PI3 kinase (phosphatidylinositol-3 kinase; PI3K)" is a lipid kinase that mediates the phosphorylation of the 3-position of the inositol ring of inositol phospholipid, which is a component of the cell membrane. Mammals are classified into four subclasses: Class IA, Class IB, Class II, and Class III. In recent years, it has been reported that activation of PI3K signals promotes maturation of oocytes (Reference 4: "Li J et al., "Activation of dormant ovarian follicles to generate mature eggs.", PNAS., Vol. 107, No. 22, p10280-10284, 2010.").

In the step (A), the inventors found that the primordial germ cells can be more efficiently differentiated into primordial follicles by performing a combination of the pressurized condition and addition of the PI3 kinase inhibitor, as shown in Examples to be described later.

Examples of the PI3K inhibitor include those that inhibit the function of PI3K. Specific examples of the PI3K inhibitor include low molecular weight compounds, PI3K expression inhibitors, and PI3K-specific binding substances.

Examples of low molecular weight compounds as the PI3K inhibitor include Pictilisib (GDC-0941) (CAS No. 957054-30-7), LY294002 (CAS No. 154447-36-6), Idelalisib (CAL-101, GS-1101) (CAS No. 870281-82-6), Buparlisib (BKM120, NVP-BKM120) (CAS No. 944396-07-0), PI-103 (CAS No. 371935-74-9), TGX-221 (CAS No. 663619-89-4), IC-87114 (CAS No. 371242-69-2), and Wortmannin (CAS No. 19545-26-7), but are not limited thereto.

Examples of the PI3K expression inhibitor include siRNA, shRNA, miRNA, ribozyme, antisense nucleic acid, and low molecular weight compounds. By administering these PI3K expression inhibitors, the expression level of the PI3K can be reduced and the PI3K signal can be suppressed. As a result, the maturation of the oocytes can be suppressed, and by further combining at least one of the pressurized condition and the low oxygen concentration condition, a state of the primordial follicle can be maintained while inducing differentiation of primordial germ cells into primordial follicles.

A small interfering RNA (siRNA) is a small double-stranded RNA of 21 base pairs or more and 23 base pairs or less used for gene silencing by RNA interference. The siRNA introduced into the cell binds to RNA-induced silencing complex (RISC). This complex binds to and cleaves mRNA with a sequence complementary to siRNA. As a result, gene expression is suppressed in a sequence-specific manner.

The siRNA can be prepared by synthesizing the sense strand and antisense strand oligonucleotides with a DNA/RNA automatic synthesizer, respectively, for example, denaturing in an appropriate annealing buffer at about 90° C. or higher and 95° C. or lower for about 1 minute, and then annealing at about 30° C. or higher and 70° C. or lower for about 1 hour or more and 8 hours or less.

SiRNAs, shRNAs, miRNAs, ribozymes and antisense nucleic acids may contain various chemical modifications to improve stability and activity. For example, in order to prevent degradation by a hydrolase such as a nuclease, a phosphate residue may be replaced with a chemically modified phosphate residue such as phosphorothioate (PS), methylphosphonate, or phosphorodithionate. Further, at least a part thereof may be configured of nucleic acid analogs such as peptide nucleic acid (PNA).

Examples of the PI3K-specific binding substance include those that specifically bind to PI3K and inhibit the function of PI3K, and examples thereof include antibodies, antibody fragments, and aptamers. The antibody can be produced, for example, by immunizing an animal such as a mouse with the PI3K protein or a fragment thereof as an antigen. Alternatively, the antibody can be prepared, for example, by screening a phage library. Examples of the antibody fragment include Fv, Fab, and scFv. The above antibody is preferably a monoclonal antibody. Moreover, a commercially available antibody may be used.

The aptamer is a substance having a specific binding ability to a target substance. Examples of the aptamer include nucleic acid aptamers and peptide aptamers. Nucleic acid aptamers having a specific binding ability to a target peptide can be selected, for example, by a systematic evolution of ligand by exponential enrichment (SELEX) method or the like. Also, the peptide aptamer having a specific binding ability to the target peptide can be selected by, for example, a Two-hybrid method using yeast.

The amount of the PI3K inhibitor added can be appropriately selected depending on the type of inhibitor to be used. For example, in a case of a low molecular weight compound (particularly, LY294002), the final concentration in the medium can be set to about 0.01 µM or higher and 300 µM or lower, and can be set to about 0.1 µM or higher and 100 µM or lower. When the amount of the PI3K inhibitor added is within the above range, the maturation of oocytes can be suppressed more effectively.

As the time at which the PI3K inhibitor is added, the conditions may be started at the start time of culturing the primordial germ cell and the supporting cell adjacent to the primordial germ cell, and may be started in the middle of culturing according to the time when the formation of the primordial follicle is started.

In addition, in the method of the present embodiment, the step (A) is carried out under the pressurized condition or the low oxygen concentration condition, and further under a condition in which an influence of estrogen or a factor having a function similar to a function of the estrogen is eliminated.

In addition, in this specification, the "estrogen" refers to a kind of sex steroid hormone, which is generated by metabolism from androgen in the granulosa cells of the ovary. The released estrogen activates transcription of a specific gene by binding to the estrogen receptor. Three types of estrogen are known, estrone (E1), estradiol (E2), and estriol (E3), and these are included when referred to as estrogen in the present specification. Further, in the present specification, the "sex steroid hormone" includes androsterone such as testosterone, dehydrotestosterone, androsterone in addition to the estrogen.

Further, in the present specification, when the expression the "factor having a function similar to a function of the estrogen" or a "factor having a function similar to the function of sex steroid hormone" is used, expression refers to that the factor has the same function as or a function similar to that of estrogen or sex steroid hormone.

Further, in the present specification, the term "function similar to estrogen" or a "function similar to sex steroid hormone" refers to the following (i) or (ii) when primordial germ cells are cultured in vitro.
   (i) Function of inhibiting disruption of oocyte cysts in oocytes derived from primordial germ cells; and
   (ii) At least one function of inhibiting the formation of primordial follicles Examples of the factor having a function similar to the function of estrogen or sex steroid hormone include factors that bind to sex steroid hormone receptors such as estrogen and androgen, and specifically, phenol red in a medium. In addition to containing the estrogen or the androgen, serum may contain factors that have a function similar to the function of unidentified estrogen, in some cases. Therefore, it is preferable that such estrogen or sex steroid hormones may be contained. It is preferable that the culture conditions are such that the influence of a factor having a function similar to the function of estrogen or sex steroid hormone can be eliminated. The term "oocyte cyst" as used herein refers to a state in which cells are connected by an intercellular bridge due to incomplete cytokinesis during the embryonic period.

Here, in the culture "under the condition in which the influence of sex steroid hormones (for example, an influence of estrogen or a factor having a function similar to a function of the estrogen) is eliminated", culture in the presence of "sex steroid hormone inhibitor" is included. In addition, one example thereof includes culturing in the presence of an "estrogen inhibitor". The "sex steroid hormone inhibitor" includes not only an estrogen inhibitor and an androgen inhibitor, but also a combination of the androgen inhibitor and the estrogen inhibitor. The "estrogen inhibitor" or "sex steroid hormone inhibitor" used in the method of the present embodiment has an action capable of inhibiting the activation of an estrogen receptor or a sex steroid hormone receptor.

Specific examples of the inhibitor include an antagonist of estrogen receptor, ICI 182,780 ((7R, 9S, 13S, 14S, 17S)-7-(9-(4,4,5,5,5-Pentafluoropentylsulfinyl)nonyl))-7,8,9,11,12,13,14,15,16,17-decahydro-13-methyl-6H-cyclopenta[a]phenanthrene-3,17-diol). Also, as specific examples of similar inhibitors, commercially available products such as tamoxifen citrate, 4-hydroxytamoxifen, MPP(4-[1-(4-hydroxyphenyl)-4-methyl-5-[4-[2-(1-piperidinyl)ethoxy]phenyl]-1H-pyrazol-3-yl]-phenol), PHTPP (4-[2-Phenyl-5,7-bis(trifluoromethyl)pyrazolo[1,5-a]pyrimidin-3-yl]phenol), G15((3aS,4R,9bR)-4-(6-Bromo-1,3-benzodioxol-5-yl)-3a,4,5,9b-3H-cyclopenta[c]quinoline) can be used.

In addition, for example, among sex steroid hormone inhibitors, as an inhibitor of androgen receptor, commercially available products such as KW-365 (N-[4-[(Benzyl)(4-nitrophenyl) amino]-1-methylpyrrole-2-carbonyl]pyrrolidine) can be used. The estrogen and sex steroid hormone inhibitors are not limited to those described above, and as long as the inhibitors have an action capable of inhibiting the activation of estrogen and sex steroid hormone receptors and can differentiate primordial germ cells into primordial follicles, the inhibitors can be used.

Inhibition of activation of estrogen and sex steroid hormone receptors by addition of estrogen and sex steroid hormone inhibitors is considered to be able to control at least one of oocyte cyst disruption and primordial follicle formation. Therefore, it is preferable that the estrogen inhibitor is added at a timing prior to the timing at which at least one of oocyte cyst disruption and primordial follicle formation occurs. In addition, it is not necessary to culture the primordial germ cells and the supporting cells adjacent to the primordial germ cells "under the condition in which the influence of sex steroid hormones (for example, an influence of estrogen or a factor having a function similar to the estrogen) is eliminated" from the start of culturing, and it is preferable to perform the culture "under the condition in which the influence of sex steroid hormones (for example, influence of the estrogen or a factor having a function similar to a function of the estrogen) is eliminated" at least when at least one of oocyte cyst disruption and primordial follicle formation occurs.

Hereinafter, a case where an estrogen inhibitor is used as a sex steroid hormone inhibitor and a mouse is used as an animal species will be described as an example. For example, in a mouse, disruption in many oocyte cysts occurs from 17.5 days before and after birth. Therefore, it is preferable to add the estrogen inhibitor from the number of days of culture corresponding to the time of such fetal age. In a case where the gonads are collected at a fetal age of 12.5 days and the culture of primordial germ cells is started from the collection day, the 5th day of in vitro culture is considered to correspond to the 17.5th day of fetal age. In addition, the culture period in a medium containing an estrogen inhibitor is preferably a period during which the disruption of oocyte cysts and the formation of primordial follicles are completed. When culturing mouse primordial germ cells, it is preferable, but not limited to, that the culture period is 6 days from the 5th day of the culture to the 11th day of the culture. In addition, when culturing the aggregates of the pluripotent stem cell-derived PGCLC and somatic cells of mouse, it is preferable, but not limited to, that the culture period is 4 days from the 7th day to the 10th day of the culture, counting from the start of the culture of the aggregates prepared in advance.

In addition, although the explanation was given using a mouse as an example, those skilled in the art would consider the time between the disruption of oocyte cysts and the formation of primordial follicles for each animal species to be used, and set the culture period of the "estrogen inhibitor", as appropriate. In addition, it is not limited to the use of "estrogen inhibitors", it is preferable that the period of culturing under "condition in which the influence of sex steroid hormones (for example, the influence of estrogen or a factor having a function similar to a function of the estrogen) is eliminated" is the period during which the disruption of oocyte cysts and the formation of primordial follicles are completed. In addition, the culture under the above condition may begin after the oocyte cysts begin to disintegrate, and may be stopped before the formation of primordial follicles is complete, as long as functional oocytes are obtained.

The estrogen inhibitor and the sex steroid hormone inhibitor can be used by adding these inhibitors to a known basal medium used for culturing primordial germ cells. Examples of such a basal medium include those similar to the basal medium exemplified above.

When, for example, ICI 182,780 is used as the estrogen inhibitor when culturing mouse primordial germ cells, it is preferable to add the ICI 182,780 to the medium within a range of 0.01 µM or higher and 50 µM or lower (final concentration), and more preferably within a range of 0.1 µM or higher and 10 µM or lower (final concentration). Those skilled in the art can appropriately adjust the timing and concentration of the addition of the estrogen inhibitor depending on the animal species from which the primordial germ cells are derived, the basal medium to be used, the estrogen inhibitor to be used, and the like. For culturing during the period in which the estrogen inhibitor is not added, the basal medium exemplified above may be used for culturing.

Also, as another method of culturing "under the condition in which the influence of sex steroid hormones (for example, the influence of estrogen or a factor having a function similar to a function of the estrogen) is eliminated", culture in a serum-free medium can be mentioned. Here, the serum-free medium may be a known serum-free medium (for example, a serum-free medium prepared so that it can be used as it is, such as StemPro (registered trademark)-34 SFM), or a serum-free medium prepared by using an alternative serum.

When preparing the serum-free medium by using the alternative serum, for example, the serum-free medium can be prepared by adding, to the basal medium, a commercially available alternative serum such as Serum Protein Substitute (SPS), KSR, serum substitute supplement (SSS) (registered trademark), instead of fetal bovine serum (FBS). As the alternative serum, SPS or KSR is preferable.

Examples of the basal medium to be used in the preparation of the serum-free medium include those similar to the basal medium exemplified above. However, the basal medium used in the step (A) is not limited to those listed above as long as the primordial germ cells differentiate into primordial follicles.

In addition, when culturing mouse primordial germ cells, for example, in a case where the SPS instead of a serum such as FBS is used as a culture condition in which the influence of sex steroid hormones (for example, the influence of estrogen or a factor having a function similar to a function of the estrogen) is eliminated, it is preferably added to the medium in a range of 5% or higher and 20% or lower (final concentration), and more preferably 10% (final concentration). Those skilled in the art can appropriately adjust the concentration of the alternative serum depending on the animal species from which the primordial germ cells are derived, the basal medium to be used, the alternative serum to be used, and the like.

In addition, the period for culturing using the serum-free medium is preferably a period during which the disruption of oocyte cysts and the formation of primordial follicles are completed. It is also possible to perform culture by using the serum-free medium from beginning to end during the culture period of the primordial germ cells in the step (A).

Those skilled in the art can appropriately adjust the timing of switching from the serum medium to the serum-free medium, as appropriate, depending on the animal species from which the primordial germ cells are derived or the serum-free medium to be used. For culturing during the period without using a serum-free medium, it is preferable to perform the culture using a medium in which a serum such as FBS is added to the basal medium listed above, but as described above, it is possible to perform the culture in a serum-free medium from beginning to end, during culturing of the gonads. The basal medium may appropriately contain other components such as ascorbic acid and penicillin as long as other components do not interfere with the differentiation of primordial germ cells into primordial follicles.

Further, it is preferable that the primordial follicle obtained by using the method of the present embodiment satisfies the following conditions of (1) and (2):
(1) an oocyte is surrounded by flat granulosa cells;
(2) a transcription factor having a function of maintaining follicle maturation in a resting phase is localized in a nucleus of the oocyte.

By satisfying the above conditions, it can be evaluated that the follicle is closer to the atomic follicle formed in the living body.

Examples of the transcription factor having a function of maintaining follicle maturation in the resting phase include Foxo3a (also referred to as Fkhr2, C76856, FKHRL1, 1110048B16Rik, and 2010203A17Rik).

Further, it is preferable that the primordial follicle obtained by using the method of the present embodiment satisfies, in addition to the conditions of (1) and (2), the following condition of (3):
(3) a diameter is 20 μm or smaller.

The conditions of (1) and (3) above can be evaluated visually using, for example, a microscope. Also, the condition of (1) above can be evaluated by immunostaining using an antibody against a protein (for example, fibronectin) expressed by granulosa cells.

The condition of (2) can be evaluated by, for example, immunostaining using an antibody (for example, an anti-Foxo3a antibody) against the transcription factor. In addition, in order to confirm that it is localized in the nucleus, for example, a commercially available nuclear staining reagent (for example, 4',6-diamidino-2-phenylindole (DAPI)) may be used in combination for the immunostaining, as necessary.

<Application of Use>

The primordial follicles obtained by using the method of the present embodiment are suitably used for infertility treatment. That is, in one embodiment, the present invention provides a method of treating an infertility using the primordial follicle obtained by the above method.

In addition, the primordial follicles obtained by using the method of the present embodiment are suitably used for efficient breeding of industrial animals and breeding of rare animals. That is, in one embodiment, the present invention provides a method of breeding industrial animals or a method of breeding rare animals using the primordial follicles obtained by the above method.

Mammals are preferable as the target animals. Mammals include those similar to those provided as exemplary examples above.

In addition, the primordial follicles obtained by using the method of the present embodiment can be useful for investigating the cause of infertility and elucidating the mechanism of menopausal diseases.

EXAMPLES

Hereinafter, the present invention will be described with reference to examples, but the present invention is not limited to the following examples.

<Experimental Material>

All animals used in examples below were purchased from Japan SLC, Inc. In addition, 12.5 day-old female mouse was obtained by mating C57BL/6 Stella-CFP transgenic mouse male with ICR mouse female. Also, all tests have been approved by the Animal Care and Use Committee of Kyushu University.

[Reference Example 1] Confirmation of Formation Process of Primordial Follicle in Mouse Living Body First, a process of primordial follicle formation in vivo was confirmed.

(1) Preparation of Tissue Section

A gonad was excised from each of female mouse 3.5 day-old and a fetus of a female mouse (12.5 days after fertilization) and a frozen section was prepared. Specifically, the gonad was immersed in PBS containing 4% paraformaldehyde and immobilized at 4° C. for 3 hours. Then, the gonad was treated stepwise with 10%, 15%, and 20% sucrose, and was embedded in an O.C.T. compound (manufactured by Tissue-Tek) and frozen. Next, a section having a thickness of 7 μm was prepared from the frozen gonad.

(2) Immunostaining

Next, a tissue section of the gonad obtained in (1) was immersed in a solution containing a 200-fold diluted mouse anti-Ddx4/MVH polyclonal antibody (manufactured by Abcam Plc.) and a 500-fold diluted rabbit anti-fibronectin antibody (manufactured by Sigma), and then subjected to a primary antibody-antigen reaction at 4° C. overnight. Then, after removing each primary antibody solution and washing with PBS, the tissue section of the gonad was immersed in solutions respectively containing a 500-fold diluted Alexa Fluor 647-labeled anti-mouse IgG antibody (Molecular robes, manufactured by Life Technologies) and a 500-fold diluted Alexa Fluor Plus 555-labeled anti-rabbit IgG antibody, and subjected to a secondary antibody-antigen reaction at a room temperature for 3 hours. Next, after removing each secondary antibody solution and washing with PBS, and the tissue section of the gonad was immersed in a solution containing a 1000-fold diluted Alexa Fluor 488-labeled Phalloidin and subjected to a reaction at a room temperature for 1 hour. Furthermore, after washing with PBS, the tissue section of the gonad was stained with 4',6-diamidino-2-phenylindole (DAPI) (manufactured by Wako Pure Chemical Industries, Ltd.).

(3) Observation

The tissue section of the gonad immunostained in (2) was observed with a confocal microscope (model number: Zeiss LSM 700, manufactured by Carl Zeiss). Results are shown in FIG. 1. In FIG. 1, a to d are immunostaining images of gonad sections of 3.5-day-old female mouse. A scale bar represents 10 μm. a is an immunostaining image using an antibody against the MVH of a germ cell marker. b is an immunostaining image using an antibody against fibronectin, which is an extracellular matrix. c is an immunostaining image using an antibody against F-actin, which is a stress fiber. In addition, d is an image in which a nuclear-staining image using DAPI is superimposed on the immunostaining images in a to c. In addition, a' to d' are magnified images of portions surrounded by squares in a to d, respectively. A scale bar represents 10 μm. e to h are immunostaining images of gonad sections of 12.5-day-old female mouse after fertilization. A scale bar represents 10 μm. e is an immunostaining image using an antibody against the MVH of a germ cell marker. f is an immunostaining image using an antibody against fibronectin, which is an extracellular matrix. g is an immunostaining image using an antibody against F-actin, which is a stress fiber. In addition, h is an image in which a nuclear-staining image using DAPI is superimposed on the immunostaining images in a to c. In addition, e' to h' which are magnified images of portions surrounded by squares in e to h, respectively.

From a to d and a' to d' in FIG. 1, there were primordial follicles covered with a flat layer of granulosa cells in the gonad of 3.5 day-old female mouse, and a developed extracellular matrix was confirmed therearound.

On the other hand, from e to h and e' to h' in FIG. 1, a developed extracellular matrix was not confirmed around the primordial germ cell in the gonad of a female mouse 12.5 days after fertilization.

The development of the extracellular matrix was consistent with accumulation of stress fiber F-actin.

[Example 1] In Vitro Culture of Primordial Germ Cell Under Pressurized Condition Then, in an in vitro culture system, an attempt was made to culture a gonad of a 12.5 day-old female mouse under an artificially pressurized condition.

(1) Preparation of Gonad and Medium

As a medium used for in vitro culture, a medium (hereinafter, this medium may be referred to as an "αM2") in which αMEM was used as a basal medium and 2% fetal bovine serum (FBS), 55 μM of 2-mercaptoethanol (2ME) (Gibco, Life Technologies), 1×penicillin/streptomycin (Gibco, Life Technologies), and 1×GlutaMax (registered trademark) (Gibco, Life Technologies) were added to the αMEM and a medium (hereinafter, this medium may be referred to as an "S10") in which StemPro (registered trademark) (Gibco, Life Technologies) was used as a basal medium and 10% FBS, 55 μM of 2ME (Gibco, Life Technologies), 1×penicillin/streptomycin (Gibco, Life Technologies), and 1×GlutaMax (registered trademark) (Gibco, Life Technologies) were added to the StemPro were prepared.

Also, the gonad used for culturing was collected from a female mouse fetus (12.5 days after fertilization) or 7.5 day-old female mouse without mesonephros.

(2) In Vitro Culture of Gonad

Then, using the medium prepared in (1), gonad collected from 12.5 day-old female mouse was cultured under an artificially pressurized condition.

Specifically, first, a Transwell-COL membrane (3.0 μm pore size, 24 mm diameter) (manufactured by Corning Inc.) was set in each well of a 6-well plate, and the gonad collected in (1) were placed on a membrane. Then, 1.3 mL of medium was added to each well and culture was performed for 21 days. For artificial pressurization, AGP-3001S (registered trademark) manufactured by STREX was used to apply a hydrostatic pressure of 33.33 kPa. Also, the medium was cultured in αM2 for 4 days and then cultured in S10. In addition, ICI 182,780 (7α,17β-[9-[(4,4,5,5,5-pentafluoropentyl)sulfinyl]nonyl]estra-1,3,5(10)-triene-3,17-diol) (manufactured by Tocris Bioscience) which is an estrogen receptor antagonist was added during the period from 5th to 9th day after the start of culture such that a final concentration in the medium is 500 nM. About half of the medium was replaced with anew medium every other day. In addition, as a control, those cultured in the same manner without pressurization (cultured under a steady condition) were also prepared.

(3) Preparation of Tissue Section

In the gonad cultured in (2), a tissue section of the gonad was prepared by using the same method as in (1) of Reference Example 1.

(4) Immunostaining

Next, immunohistochemical staining was performed on the tissue section of the gonad obtained in (3). Specifically, first, the tissue section of the gonad was immersed in solutions respectively containing a 200-fold diluted mouse anti-Ddx4/MVH polyclonal antibody (manufactured by Abcam) and a 200-fold diluted rabbit anti-Foxo3a polyclonal antibody (manufactured by Cell Signaling Technologies) and was subjected to a primary antibody-antigen reaction at 4° C. overnight. Then, after removing each primary antibody solution and washing with PBS, the tissue section of the gonad was immersed in solutions respectively containing a 500-fold diluted Alexa Fluor 647-labeled anti-mouse IgG antibody (Molecular robes, manufactured by Life Technologies) and a 500-fold diluted Alexa Fluor Plus 555-labeled anti-rabbit IgG antibody (molecular robes, manufactured by Life Technologies), and subjected to a secondary antibody-antigen reaction at a room temperature for 3 hours. Then, after removing each secondary antibody solution and washing with PBS, the tissue section of the gonad was further stained with 4',6-diamidino-2-phenylindole (DAPI) (manufactured by Wako Pure Chemical Industries, Ltd.).

(5) Observation

Figure 2:
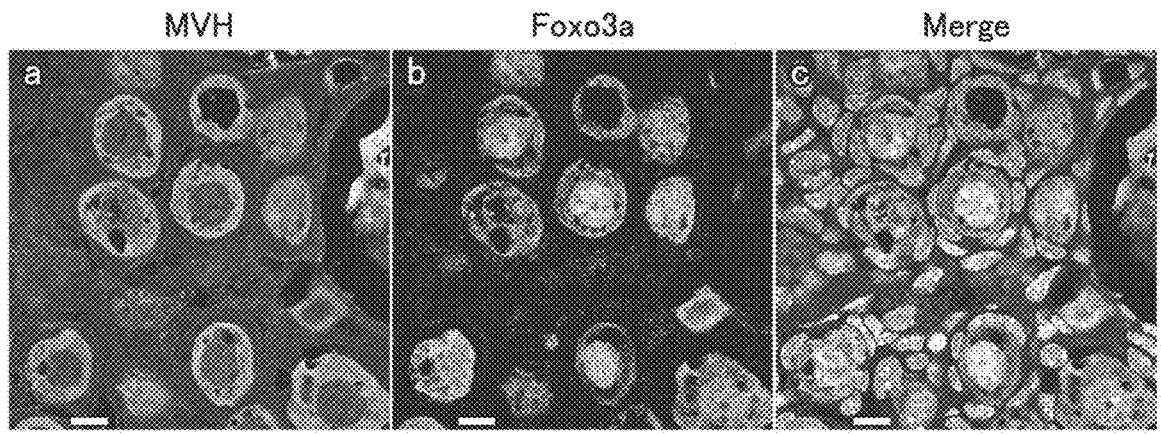
FIG. 2 shows a to c which are immunostaining images of gonad sections which were obtained by culturing gonads of 12.5 day-old female mouse after the fertilization under a pressurized condition and collecting the gonad sections on the 21st day from the start of the culturing in Example 1. a is an immunostaining image using an antibody against the MVH of a germ cell marker. b is an immunostaining image using an antibody against a transcription factor Foxo3a. c is an image in which a nuclear-staining image using DAPI is superimposed on the immunostaining images in a and b. A scale bar represents 10 μm.

The tissue section of the gonad immunostained in (4) was observed with a confocal microscope (model number: Zeiss LSM 700, manufactured by Carl Zeiss). FIG. 2 shows typical results of the gonad cultured under the pressurized condition. In FIG. 2, a to c are immunostaining images of gonad sections which were obtained by culturing gonads of 12.5 day-old female mice after the fertilization under a pressurized condition and collecting the gonad sections on the 21st day from the start of the culturing. The magnification is 63 times. a is an immunostaining image using an antibody against the MVH of a germ cell marker. b is an immunostaining image using an antibody against a transcription factor Foxo3a. c is an image in which a nuclear-staining image using DAPI is superimposed on the immunostaining images in a and b. A scale bar represents 10 µm.

Figure 3:
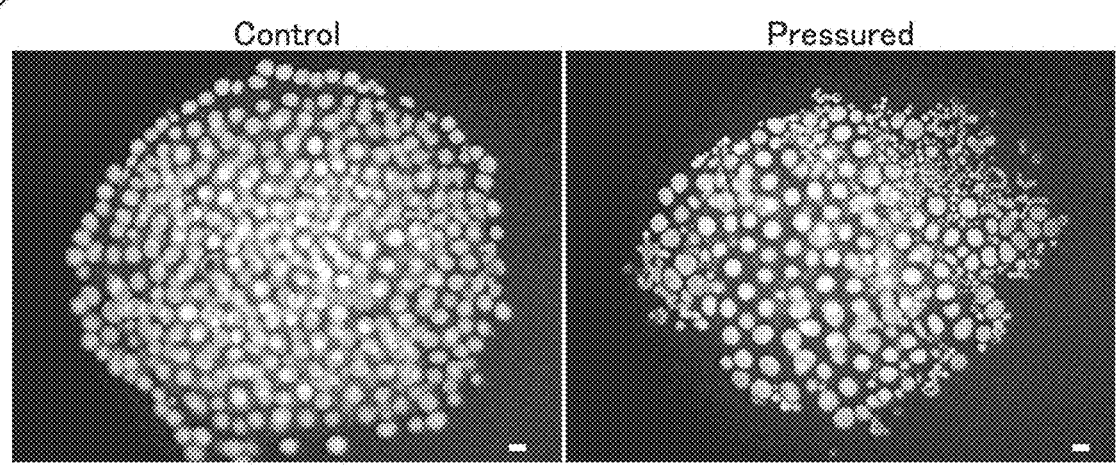
FIG. 3 shows captured images, taken by a fluorescent stereomicroscope, of gonad sections which were obtained by culturing gonads of 12.5 day-old female mouse after the fertilization under a steady condition (Control) or a pressurized condition (Pressured) and collecting the gonad sections on the 21st day from the start of the culturing in Example 1. Oocytes were visualized by fluorescence of a cyan fluorescent protein (CFP) expressed under a control of expression of Stella, which is an oocyte marker. A scale bar represents 50 μm.

Further, FIG. 3 shows captured images taken by a fluorescent stereomicroscope (manufactured by Olympus Corporation, model number: SZX16) before producing a section of the gonad cultured in (2). In FIG. 3, "Control" is a gonad cultured under the steady condition, and "Pressured" is a gonad cultured under the pressurized condition. A scale bar represents 50 µm.

From FIG. 3, it was found that, on the 21st day after culturing, most of the primordial germ cells were differentiated into grown secondary follicles in the gonad cultured under the steady condition. On the other hand, it was revealed that small follicles of 20 µm or smaller were present in the gonad cultured under the pressurized condition.

A tissue section of this small follicle was prepared and examined in detail by immunostaining. As a result, it was confirmed that the section was surrounded by more flat granulosa cells and the transcription factor Foxo3a was localized in the nucleus of an egg (see a to c in FIG. 2).

These results suggest that differentiation was induced from the primordial germ cell to the primordial follicle under the pressurized condition.

(6) Proteolytic Enzyme (CTK) Treatment Test

Next, an attempt was made to treat the gonad of 7.5-day-old female mouse with a proteolytic enzyme (CTK) under an artificially pressurized condition.

(6-1) Proteolytic Enzyme (CTK) Treatment

Specifically, first, a gonad of 7.5-day-old female mouse was cultured for 1 hour by adding 0.5 mL of PBS (containing CTK) to each well of a 6-well plate. A composition of the CTK is 1 µM $CaCl_2$), 0.1 mg/mL Collagenase IV, 20% KSR (Invitrogen), and 0.025% Trypsin EDTA (Invitrogen). For artificial pressurization, AGP-3001S (registered trademark) manufactured by STREX was used to apply a hydrostatic pressure of 33.33 kPa. In addition, as controls, a gonad cultured in PBS without containing CTK for 1 hour without performing the artificial pressurization and a gonad cultured in PBS containing CTK for 1 hour without performing the artificial pressurization were prepared.

(6-2) Preparation of Tissue Section

In the gonad CTK treated in (6-1), a tissue section of the gonad was prepared by using the same method as in (1) of Reference Example 1.

(6-3) Immunostaining

Next, immunohistochemical staining was performed on the tissue section of the gonad obtained in (3).

(6-4) Observation

Figure 4A:
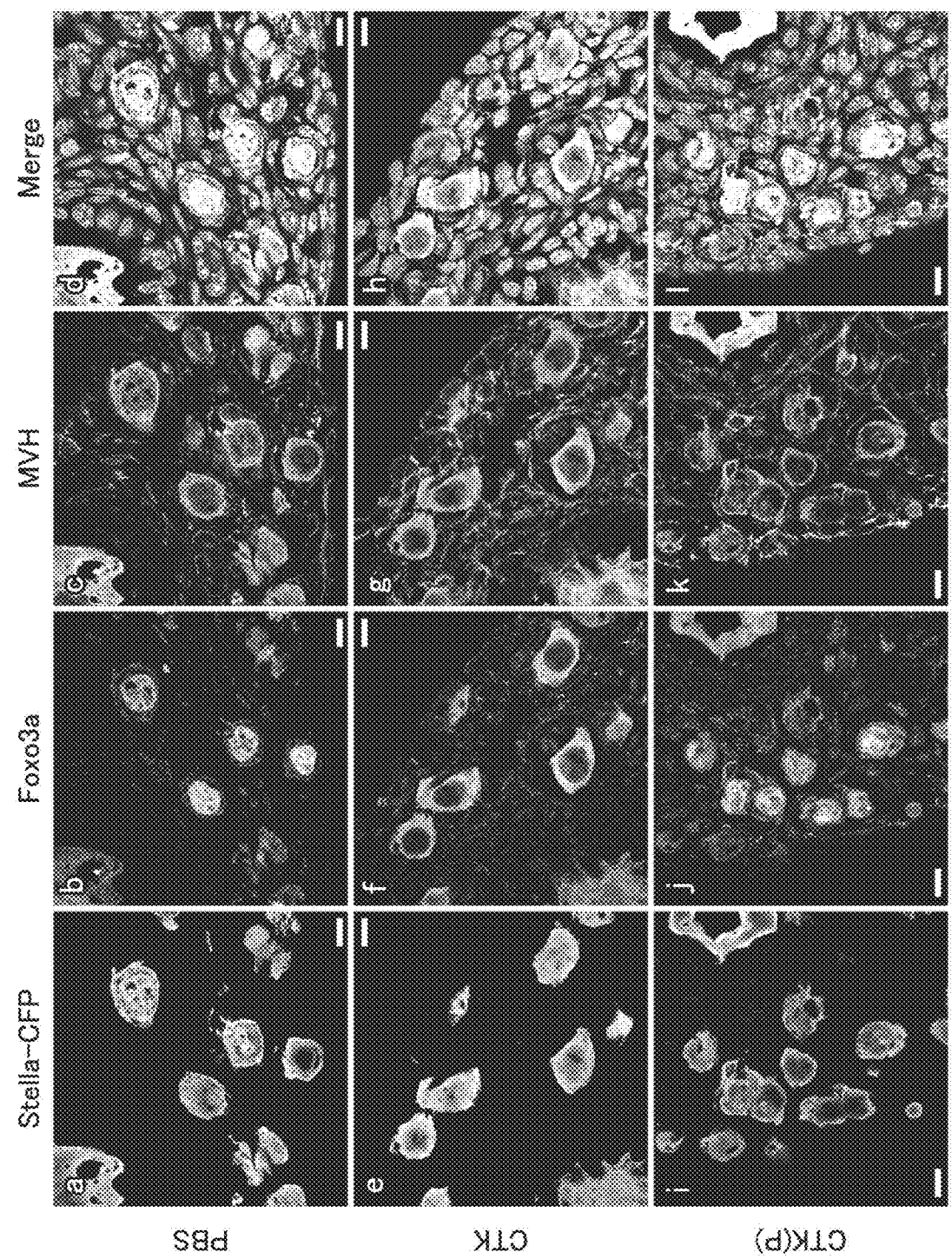
FIG. 4A shows immunostaining images of immobilized gonads of 7.5 day-old female mouse obtained by performing phosphate saline (PBS), proteolytic enzyme treatment (CTK), and proteolytic enzyme treatment under a pressurized condition (CTK (P)) for one hour in Example 1. a, e, and i are staining images for CFP expressed under the control of the expression of the germ cell marker Stella. b, f, and j are immunostaining images using an antibody against the transcription factor Foxo3a. c, g, and k are immunostaining images using an antibody against the MVH of the germ cell marker. d is an image in which a nuclear-staining image using DAPI is superimposed on the staining images in a to c. h is an image in which a nuclear-staining image using DAPI is superimposed on the staining images in e to g. l is an image in which a nuclear-staining image using DAPI is superimposed on the staining images in i to k. A scale bar represents 10 μm.

The tissue section of the gonad immunostained in (6-3) was observed with a confocal microscope (model number: Zeiss LSM 700, manufactured by Carl Zeiss). The results are shown in FIG. 4A. In FIG. 4A, "PBS" is a gonad cultured in PBS without containing CTK for 1 hour without performing the artificial pressurization. "CTK" is a gonad cultured in PBS containing CTK for 1 hour without performing the artificial pressurization. "CTK (P)" is a gonad cultured in PBS containing CTK for 1 hour under the artificial pressurized condition. a, e, and i are staining images for CFP expressed under the control of the expression of the germ cell marker Stella. b, f, and j are immunostaining images using an antibody against the transcription factor Foxo3a. c, g, and k are immunostaining images using an antibody against the MVH of the germ cell marker. d is an image in which a nuclear-staining image using DAPI is superimposed on the staining images in a to c. h is an image in which a nuclear-staining image using DAPI is superimposed on the staining images in e to g. l is an image in which a nuclear-staining image using DAPI is superimposed on the staining images in i to k. A scale bar represents 10 µm.

Figure 4B:
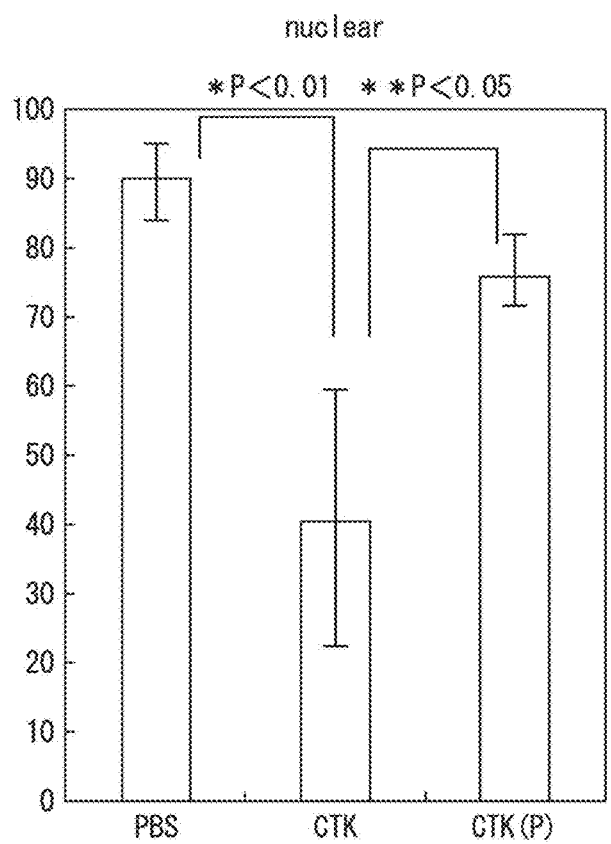
FIG. 4B is a graph showing a proportion of oocytes that localizes the transcription factor Foxo3a in the immobilized gonads of 7.5 day-old female mouse obtained by performing phosphate saline (PBS), proteolytic enzyme treatment (CTK), and proteolytic enzyme treatment under a pressurized condition (CTK (P)) for one hour in Example 1.

Further, FIG. 4B is a graph obtained by calculating a proportion of oocytes in which the transcription factor Foxo3a is localized in the nucleus, from the immunostaining image using the antibody against the transcription factor Foxo3a in FIG. 4A.

From FIGS. 4A and 4B, it was revealed that digestion of extracellular matrix by treating the gonad of 7.5-day-old female mouse with proteolytic enzymes (CTK) causes the Foxo3a of a primordial follicle egg to translocate to an outside of the nucleus and follicle maturation to be induced. Furthermore, it was revealed that this extranuclear translocation of the Foxo3a can be suppressed by performing the same proteolytic enzyme treatment under the artificially pressurized condition.

These results suggest that physical pressure is involved in the maintenance of primordial follicles in vivo.

[Example 2] In Vitro Culture of Primordial Germ Cell Under Low Oxygen Concentration Condition Next, in an in vitro culture system, an attempt was made to culture a gonad of a 12.5 day-old fetus after fertilization under a low oxygen concentration condition.

(1) Preparation of Gonad and Medium

The gonad and a medium were prepared using the same method as in (1) of Example 1.

(2) In Vitro Culture of Gonad

The gonad were in vitro cultured using the same method as in (2) of Example 1 except that the gonad was cultured under a low oxygen concentration condition instead of the artificially pressurized condition. In addition, for the low oxygen concentration condition, culturing was performed under a 5% oxygen concentration condition using APM30D manufactured by Astec. As a control, those cultured in the same manner without the low oxygen concentration condition were also prepared.

(3) Preparation of Tissue Section

In the gonad cultured in (2), a tissue section of the gonad was prepared by using the same method as in (1) of Reference Example 1.

(4) Immunostaining

Then, the tissue section of the gonad obtained in (3) was immunostained using the same method as in (4) of Example 1.

(5) Observation

Figure 5:
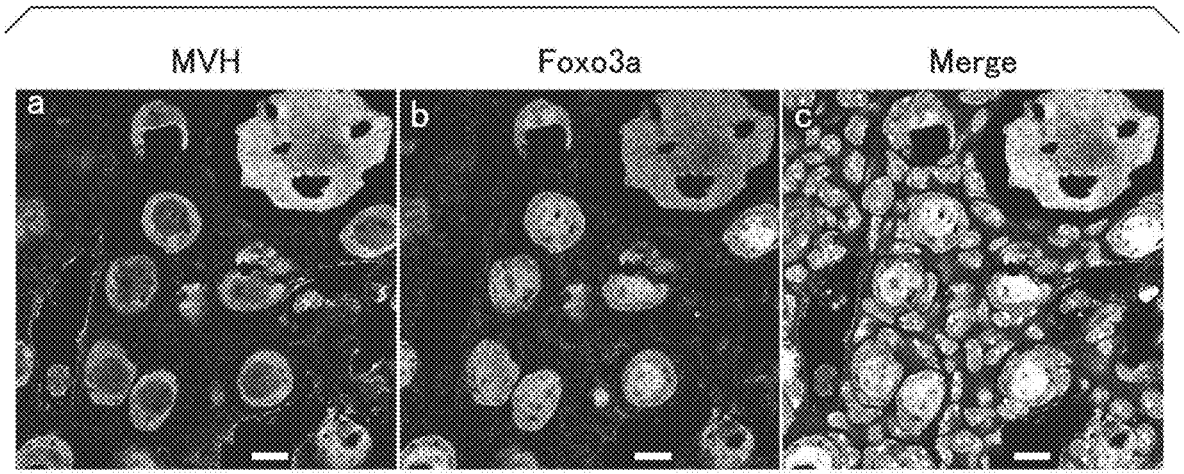
FIG. 5 shows a to c which are immunostaining images of gonad sections which were obtained by culturing gonads of 12.5 day-old female mouse after the fertilization under a low oxygen concentration condition and collecting the gonad sections on the 21st day from the start of the culturing in Example 2. a is an immunostaining image using an antibody against the MVH of a germ cell marker. b is an immunostaining image using an antibody against a transcription factor Foxo3a. c is an image in which a nuclear-staining image using DAPI is superimposed on the immunostaining images in a and b. A scale bar represents 10 μm.

The tissue section of the gonad immunostained in (4) was observed with a confocal microscope (model number: Zeiss LSM 700, manufactured by Carl Zeiss). FIG. 5 shows typical results of the gonad cultured under the low oxygen concentration condition. In FIG. 5, a to c are immunostaining images of gonad sections which were obtained by culturing gonads of 12.5 day-old female mice after the fertilization under the low oxygen concentration condition and collecting the gonad sections on the 21st day from the start of the culturing. The magnification is 63 times. a is an immunostaining image using an antibody against the MVH of a germ cell marker. b is an immunostaining image using an antibody against a transcription factor Foxo3a. c is an image in which a nuclear-staining image using DAPI is superimposed on the immunostaining images in a and b. A scale bar represents 10 µm.

It was found that, the 21st day from the start of the culture, most of the primordial germ cells were differentiated into grown secondary follicles in the gonad cultured under a normal oxygen concentration condition (not shown). On the other hand, it was revealed that small follicles of 20 μm or smaller were present in the gonad cultured under the low oxygen concentration condition. A tissue section of this small follicle was prepared and examined in detail by immunostaining. As a result, it was confirmed that the section was surrounded by more flat granulosa cells and the transcription factor Foxo3a was localized in the nucleus of an egg (see a to c in FIG. 5).

These results suggest that differentiation was induced from the primordial germ cell to the primordial follicle under the low oxygen concentration condition.

[Reference Example 2] In Vitro Culture of Primordial Germ Cell in Presence of PI3K Inhibitor Next, in an in vitro culture system, an influence of culturing a gonad of a 12.5 day-old fetus after fertilization in the presence of a PI3K inhibitor was confirmed.
(1) Preparation of Gonad and Medium
The gonad and a medium were prepared using the same method as in (1) of Example 1.
(2) In Vitro Culture of Gonad
First, a Transwell-COL membrane (3.0 μm pore size, 24 mm diameter) (manufactured by Corning Inc.) was set in each well of a 6-well plate, and the gonad collected in (1) were placed on a membrane. Then, 1.3 mL of medium was added to each well and culture was performed for 16 days. Also, the medium was cultured in αM2 for 4 days and then cultured in S10. In addition, the PI3K inhibitor LY294002 (hereinafter, may be abbreviated as "Ly") (manufactured by Cell Signaling Technology, model number: 9901) was added to the medium such that a final concentration is 25 μM, during the period from the 6th day to the 16th day from the start of the culture. In addition, ICI 182,780 (7α,17β-[9-[(4,4,5,5,5-pentafluoropentyl)sulfinyl]nonyl]estra-1,3,5(10)-triene-3,17-diol) (manufactured by Tocris Bioscience) which is an estrogen receptor antagonist was added during the period from 5th to 9th day after the start of culture such that a final concentration in the medium is 500 nM. About half of the medium was replaced with a new medium every other day. In addition, as a control, those cultured in the same manner without adding Ly (cultured under a steady condition) were also prepared.
(3) Observation The gonad on the 16th day from the start of culture were observed under a fluorescent stereomicroscope (manufactured by Olympus Corporation, model number: SZX16). The results are shown in FIG. 6A. In FIG. 6A, "Control" is a gonad cultured under a steady condition (in the absence of Ly), and "Ly" is a gonad cultured in the presence of the PI3K inhibitor LY294002. A scale bar represents 50 μm.

Figure 6B:
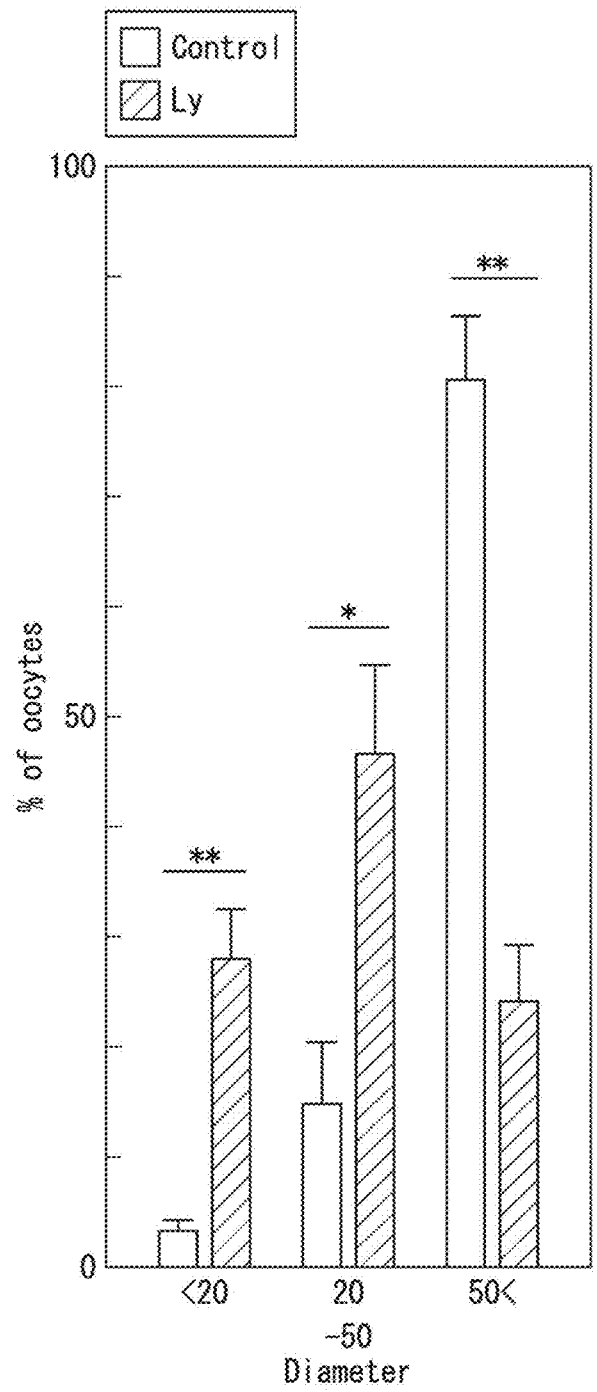
FIG. 6B is a graph showing a proportion of oocytes of each size calculated by counting the number of oocytes using the expression of Stella-CFP as an index using the fluorescence images shown in FIG. 6A.

Further, FIG. 6B is a graph in which the number of oocytes was counted using the expression of Stella-CFP as an index in FIG. 6A, and proportions of the oocytes smaller than 20 μm, 20 μm or larger and 50 μm or smaller, and larger than 50 μm were calculated.

From FIG. 6A, it was found that, on the 16th day after culturing, most of the primordial germ cells were differentiated into grown secondary follicles in the gonad cultured under the steady condition (in the absence of Ly). On the other hand, it was revealed that small follicles of smaller than 20 μm were present in the gonad cultured in the presence of Ly.

From FIG. 6B, in the gonad cultured under the steady condition (in the absence of Ly), the proportion of oocytes having a size smaller than 20 μm in total oocytes was about 5%, the proportion of oocytes with a size of 20 μm or larger and 50 μm or smaller was about 15%, and the proportion of the oocytes having a size larger than 50 μm was about 80%, and there were many oocytes larger than 50 μm. In contrast, it was confirmed that in the gonad cultured in the presence of Ly, the proportion of oocytes having a size smaller than 20 μm in total oocytes was about 29%, the proportion of oocytes with a size of 20 μm or larger and 50 μm or smaller was about 48%, and the proportion of the oocytes having a size larger than 50 μm was about 23%, and there are many follicles smaller than those under the steady condition.

[Example 3] In Vitro Culture of Primordial Germ Cell Under Pressurized Condition and in Presence of PI3K Inhibitor Then, in an in vitro culture system, an attempt was made to culture a gonad of a 12.5 day-old female mouse under the artificially pressurized condition and in the presence of the PI3K inhibitor.
(1) Preparation of Gonad and Medium
The gonad and a medium were prepared using the same method as in (1) of Example 1.
(2) In Vitro Culture of Gonad
Then, using the medium prepared in (1), gonad collected from 12.5 day-old female mouse was cultured under an artificially pressurized condition and in the presence of the PI3K inhibitor.

Figure 7:
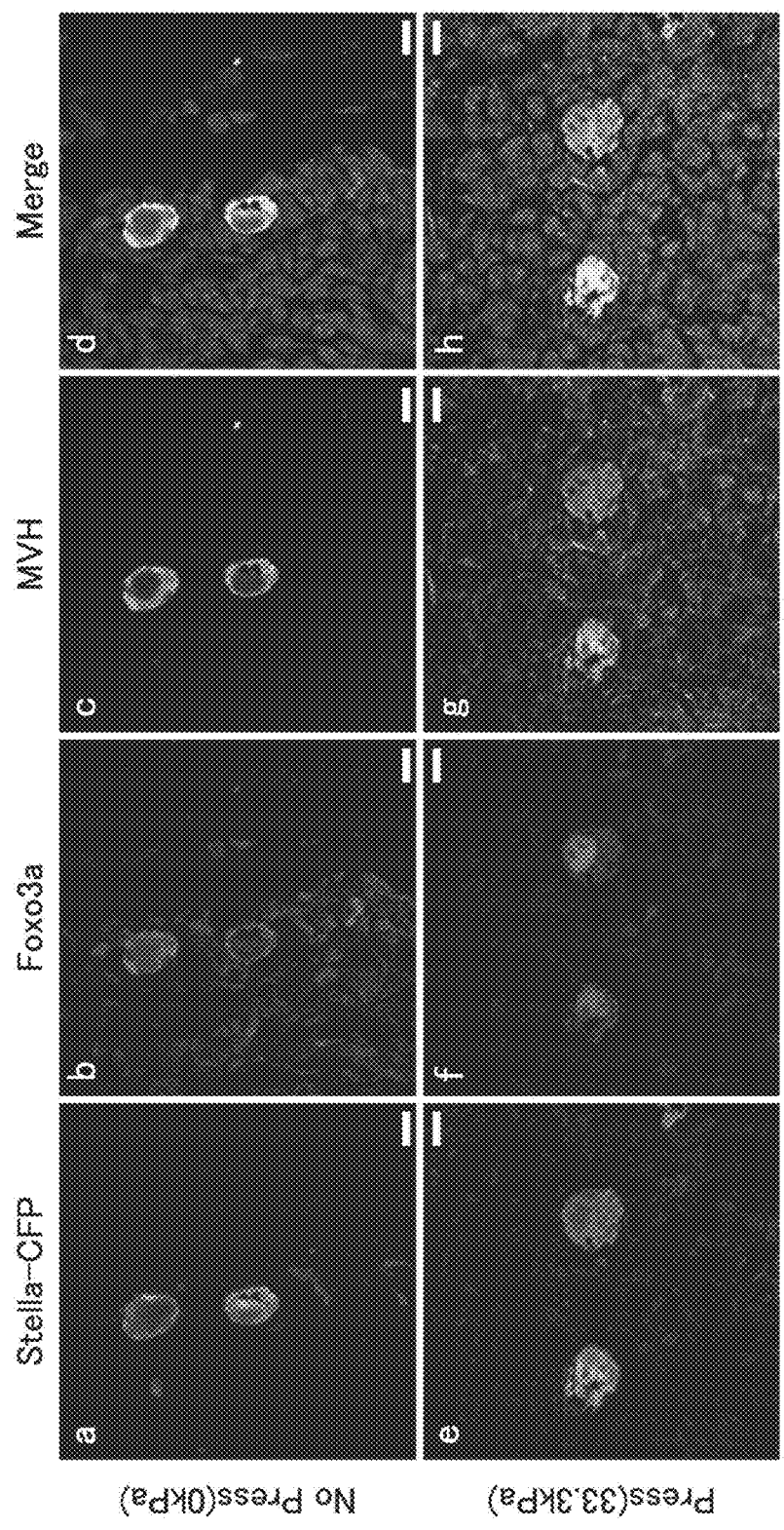
FIG. 7 shows immunostaining images of gonad sections which were obtained by culturing gonads of 12.5 day-old female mouse after fertilization, adding Ly from 6th day from the start of the culturing, further culturing the gonads under the pressurized condition (Press (33.3 kPa)), and collecting the gonad sections on the 16th day from the start of the culturing in Example 3. a and e are staining images for CFP expressed under the control of the expression of the germ cell marker Stella. b and f are immunostaining images using an antibody against a transcription factor Foxo3a. c and g are immunostaining images using an antibody against the MVH of the germ cell marker. d is an image in which a nuclear-staining image using DAPI is superimposed on the staining images in a to c. h is an image in which a nuclear-staining image using DAPI is superimposed on the staining images in e to g. A scale bar represents 10 μm.

Specifically, first, a Transwell-COL membrane (3.0 μm pore size, 24 mm diameter) (manufactured by Corning Inc.) was set in each well of a 6-well plate, and the gonad collected in (1) were placed on a membrane. Then, 1.3 mL of medium was added to each well and culture was performed for 16 days. For artificial pressurization, AGP-3001S (registered trademark) manufactured by STREX was used to apply a hydrostatic pressure of 33.33 kPa, during the period from the 6th day to the 16th day from the start of the culture. In addition, Ly was added to the medium such that a final concentration is 25 μM, during the period from the 6th day to the 16th day from the start of the culture. Also, the medium was cultured in αM2 for 4 days and then cultured in S10. In addition, ICI 182,780 (7α,17β-[9-[(4,4,5,5,5-pentafluoropentyl)sulfinyl]nonyl]estra-1,3,5(10)-triene-3,17-diol) (manufactured by Tocris Bioscience) which is an estrogen receptor antagonist was added during the period from 5th to 9th day after the start of culture such that a final concentration in the medium is 500 nM. About half of the medium was replaced with anew medium every other day. As a control, those cultured in the same manner in the presence of Ly without pressurization were also prepared.
(3) Preparation of Tissue Section
In the gonad cultured in (2), a tissue section of the gonad was prepared by using the same method as in (1) of Reference Example 1.
(4) Immunostaining
Then, the tissue section of the gonad obtained in (3) was immunohistochemically stained using the same method as in (4) of Example 1.
(5) Observation The tissue section of the gonad immunostained in (4) was observed with a confocal microscope (model number: Zeiss LSM 700, manufactured by Carl Zeiss). Results are shown in Table 7. In FIG. 7, "No Press (0 kPa)" is a gonad cultured in the presence of Ly without pressurization. "Press (33.3 kPa)" is a gonad cultured under the artificially pressurized condition and in the presence of Ly. a and e are staining images for CFP expressed under the control of the expression of the germ cell marker Stella. b and f are immunostaining images using an antibody against a transcription factor Foxo3α. c and g are immunostaining images using an antibody against the MVH of the germ cell marker. d is an image in which a nuclear-staining image using DAPI is superimposed on the staining images in a to c. h is an image in which a nuclear-staining image using DAPI is superimposed on the staining images in e to g. A scale bar represents 10 μm.

Figure 8A:
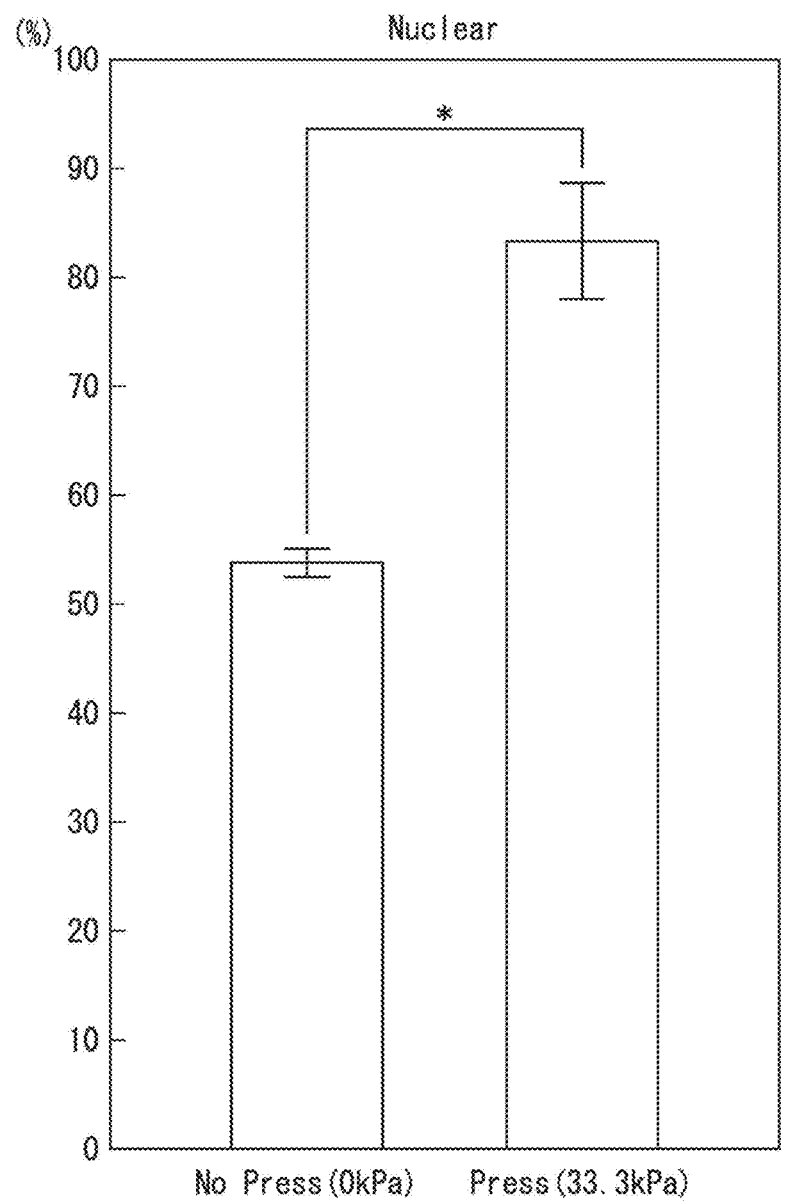
FIG. 8A is a graph showing a proportion of oocytes that localizes the transcription factor Foxo3a in a cell nucleus in the oocytes of 20 μm or smaller by analyzing the immunostaining images shown in b and f of FIG. 7.
Figure 8B:
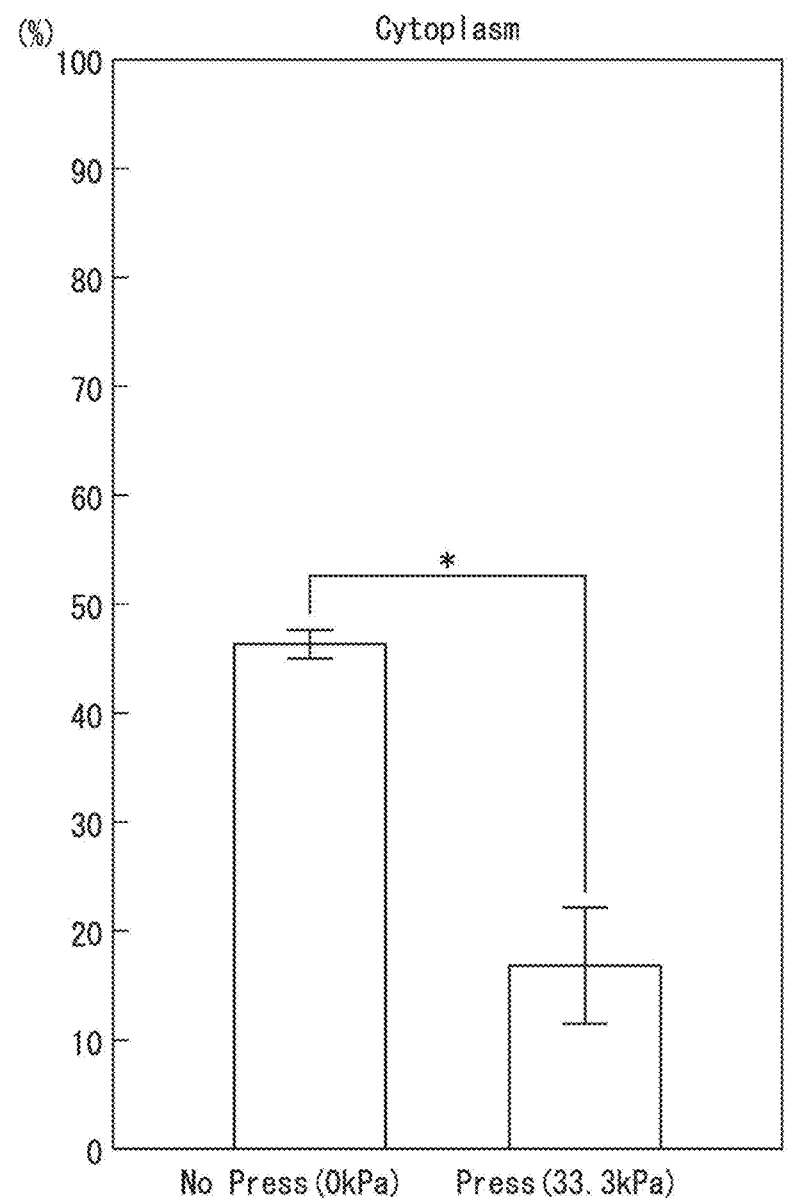
FIG. 8B is a graph showing a proportion of oocytes that localizes the transcription factor Foxo3a in a cytosol in the oocytes of 20 μm or smaller by analyzing the immunostaining images shown in b and f of FIG. 7.

Further, FIG. 8A is a graph obtained by calculating a proportion of oocytes in which the transcription factor Foxo3a is localized in the nucleus, from the immunostaining image using the antibody against the transcription factor Foxo3a in FIG. 7. FIG. 8B is a graph obtained by calculating a proportion of oocytes in which the transcription factor Foxo3a is localized in a cytosol, from the immunostaining image using the antibody against the transcription factor Foxo3a in FIG. 7.

From FIG. 7, in the gonad cultured in the presence of Ly without pressurization, the oocyte was surrounded by a layer of flat granulosa cells, but the transcription factor Foxo3a was localized not only in the nucleus of the egg but also in the cytosol. On the other hand, it was confirmed that in the gonad cultured under the artificially pressurized condition and in the presence of Ly, the oocyte was surrounded by more flat granulosa cells, and the transcription factor Foxo3a was localized in the nucleus of the egg.

From FIGS. 8A and 8B, in the gonad cultured in the presence of Ly without pressurization, the proportion of oocytes in which the transcription factor Foxo3a was localized in the nucleus was about 52%, and the proportion of oocyte in which the transcription factor was localized in the cytosol was about 48%. On the other hand, it was revealed that, in the gonad cultured under the artificially pressurized condition and in the presence of Ly, the proportion of oocytes in which the transcription factor Foxo3a was localized in the nucleus was about 82%, and the proportion of oocyte in which the transcription factor was localized in the cytosol was about 18%, and the extranuclear migration of Foxo3a was suppressed.

[Example 4] In Vitro Culture of Primordial Germ Cell Under Pressurized Condition and Low Oxygen Concentration Condition Next, in an in vitro culture system, an attempt was made to culture a gonad of a 12.5 day-old fetus after fertilization under the artificially pressurized condition and the low oxygen concentration condition.
(1) Preparation of Gonad and Medium
The gonad and a medium were prepared using the same method as in (1) of Example 1.
(2) In Vitro Culture of Gonad
The gonad were in vitro cultured using the same method as in (2) of Example 1 except that the gonad was cultured under the artificially pressurized condition and the low oxygen concentration condition. For artificial pressurization, AGP-3001S (registered trademark) manufactured by STREX was used to apply a hydrostatic pressure of 33.33 kPa. In addition, for the low oxygen concentration condition, culturing was performed under a 5% oxygen concentration condition using APM30D manufactured by Astec. As controls, (1) 3.5-day-old ovaries, (2) those similarly cultured under the artificially pressurized condition, and (3) those similarly cultured under the low oxygen concentration condition were also prepared.

Figure 9:
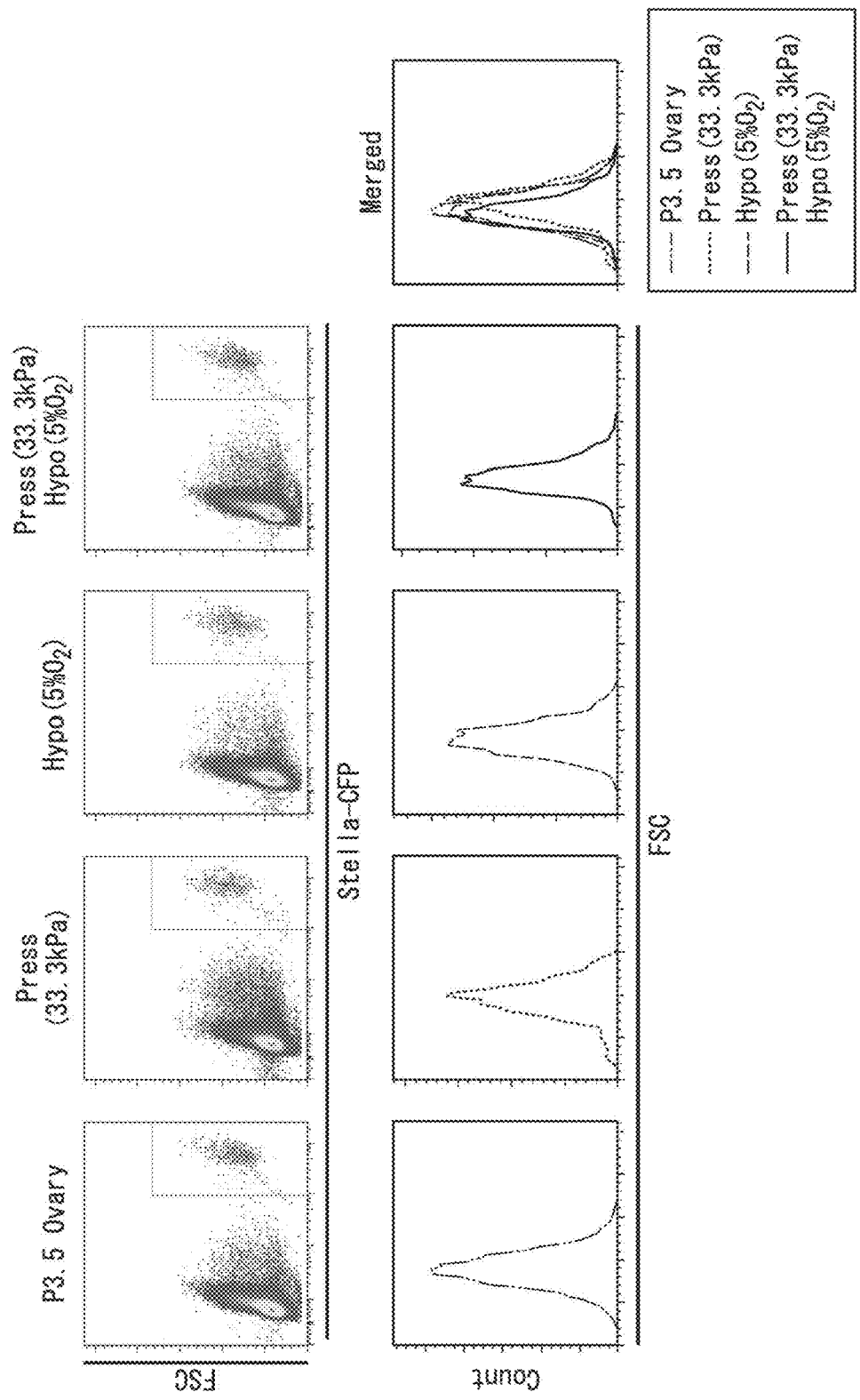
FIG. 9 is a graph showing results of a flow cytometry analysis of gonad sections obtained by culturing 3.5-day-old ovaries and a gonad of 12.5-day-old female mouse after fertilization under each condition and collecting the gonad sections on the 21st day from the start of the culturing in Example 4. The upper row shows a two-dimensional histogram of forward scattered light (FSC) indicating a cell size and fluorescence of CFP expressed under the control of the germ cell marker Stella. The lower row shows a histogram showing a distribution of FSC in CFP-expressing cells. The "Merge" at the right end of the lower row shows a histogram in which four histograms in the lower row are superposed.

(3) Flow Cytometry
The gonad cultured in (2) were crushed to prepare a cell suspension. Then, the analysis was performed using a flow cytometer (model number: BD FACSAria III (648282B5), manufactured by BD Bioscience). Results are shown in FIG. 9. The upper row shows a two-dimensional histogram of forward scattered light (FSC) indicating a cell size and fluorescence of CFP expressed under the control of the germ cell marker Stella. The lower row shows a histogram showing a distribution of FSC in CFP-expressing cells. The "Merge" at the right end of the lower row shows a histogram in which four histograms in the lower row are superposed.

Each gonad was observed with a fluorescent stereomicroscope (manufactured by Olympus Corporation, model number: SZX16) before performing flow cytometry. As a result, it was found that even under the artificial pressurized condition and the low oxygen concentration condition, differentiation was induced from the primordial germ cell to the primordial follicle, as in the case under the artificially pressurized condition or in the low oxygen concentration condition (not shown).

Further, from FIG. 9, in the gonad cultured under the artificial pressurized condition or the low oxygen concentration condition, oocytes having the same size as the ovary 3.5 day-old were obtained. On the other hand, in the gonad cultured under the artificial pressurized condition and the low oxygen concentration condition, the proportion of oocytes smaller than the ovary 3.5 day-old tended to increase.

From the above, it was clarified that the method of the present embodiment reproduces the environment in the living gonad and can differentiate the primordial germ cell into a primordial follicle.

INDUSTRIAL APPLICABILITY

According to the method of the present embodiment, it is possible to differentiate a primordial germ cell into a primordial follicle in vitro. The primordial follicle obtained by the method of the present embodiment is suitably used for, for example, an infertility treatment, efficient breeding of industrial animals, breeding of rare animals, investigation of causes of infertility, elucidation of a mechanism of menopausal diseases, and the like.

The invention claimed is:
1. A method of differentiating a primordial germ cell into a primordial follicle in vitro, the method comprising:
   culturing a primordial germ cell and a supporting cell adjacent to the primordial germ cell under a pressurized condition of between 23 kPa and 40 kPa, or an atmospheric oxygen concentration of 7% or lower.
2. The method according to claim 1,
   wherein the culturing is carried out under the pressurized condition and atmospheric oxygen concentrations.
3. The method according to claim 1,
   wherein the culturing is carried out in the presence of a PI3 kinase inhibitor.
4. The method according to claim 3, wherein the PI3 kinase inhibitor is LY294002.
5. The method according to claim 1, wherein the culturing is carried out in the presence of an estrogen inhibitor.
6. The method according to claim 1, wherein the low oxygen concentration condition is a condition in which an oxygen concentration in a culture atmosphere is between 3% and 7%.

7. The method according to claim 1, wherein the pressurized condition is between 28 kPa and 38 kPa.

8. The method according to claim 1, wherein the obtained primordial follicle is formed of flat granulosa cells and an oocyte surrounded by the flat granulosa cells, and
a Foxo3a is localized in the nucleus of the oocyte.

9. The method according to claim 8, wherein the obtained primordial follicle has a diameter of 20 μm or smaller.

* * * * *